(12) United States Patent
Daubresse et al.

(10) Patent No.: US 8,328,880 B2
(45) Date of Patent: Dec. 11, 2012

(54) METHOD OF COLOURING AND LIGHTENING KERATIN MATERIALS IN THE PRESENCE OF A REDUCING AGENT COMPRISING A FLUORESCENT DISULPHIDE DYE

(75) Inventors: Nicolas Daubresse, St Cloud (FR); Andrew Greaves, Montevrain (FR); Henri Samain, Bievres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/232,452

(22) Filed: Sep. 14, 2011

(65) Prior Publication Data
US 2012/0177587 A1  Jul. 12, 2012

Related U.S. Application Data

(62) Division of application No. 12/282,586, filed as application No. PCT/FR2007/051008 on Mar. 23, 2007, now Pat. No. 8,038,731.

(60) Provisional application No. 60/792,941, filed on Apr. 19, 2006.

(30) Foreign Application Priority Data

Mar. 24, 2006 (FR) .................................. 06 51035

(51) Int. Cl.
*A61Q 5/10* (2006.01)
(52) U.S. Cl. ............. 8/405; 8/426; 8/432; 8/435; 8/465; 8/587; 8/648; 132/202; 132/208
(58) Field of Classification Search .............. 8/405, 426, 8/432, 435, 465, 587, 648; 132/202, 208
See application file for complete search history.

(56) References Cited

U.S. PATENT DOCUMENTS 7,488,354 B2 * 2/2009 Daubress et al. ................. 8/405

OTHER PUBLICATIONS

STIC Search Report dated Jun. 11, 2012.*

* cited by examiner

*Primary Examiner* — Eisa Elhilo
(74) *Attorney, Agent, or Firm* — O'Brien Jones, PLLC.

(57) ABSTRACT

The invention relates to a dyeing composition comprising a fluorescent disulfide dye and to a method of dyeing keratin materials, with a lightening effect, that employs said composition. It likewise relates to new fluorescent disulfide dyes and to their uses in the lightening of keratin materials. The composition allows a particularly persistent lightening effect to be obtained.

15 Claims, No Drawings

METHOD OF COLOURING AND LIGHTENING KERATIN MATERIALS IN THE PRESENCE OF A REDUCING AGENT COMPRISING A FLUORESCENT DISULPHIDE DYE

This application is a divisional application of U.S. application Ser. No. 12/282,586 filed on Jul. 1, 2009, now a U.S. Pat. No. 8,038,731 B2, which is a National Phase application based on PCT/FR2007/051008 filed on Mar. 23, 2007, and which claims the priority of French Application No. 0651035, filed on Mar. 24, 2006, and the benefit of U.S. Provisional Application No. 60/792,941, filed on Apr. 19, 2006.

The invention relates to a method of colouring and lightening keratin materials in the presence of a reducing agent.

Dyeing of keratin fibres, particularly human keratin fibres, by direct dyeing is known. The method conventionally used in direct dyeing involves applying direct dyes to the keratin fibres, said dyes being coloured and colouring molecules which have an affinity for the fibres, allowing said dyes to diffuse, and then rinsing the fibres.

The direct dyes which are conventionally used are, for example, nitrobenzene dyes, anthraquinone dyes, nitropyridine dyes or azo, xanthene, acridine, azine or triarylmethane dyes.

The dyeings which result from the use of direct dyes are temporary or semi-permanent dyeings, since the nature of the interactions that bind the direct dyes to the keratin fibre, and their desorption from the surface and/or from the core of the fibre, are responsible for their weak dyeing power and their poor fastness to washing or perspiration.

Furthermore, the dyeing of keratin fibres on the basis of conventional direct dyes does not allow the keratin fibres to be significantly lightened.

The lightening of the colour of keratin fibres, more particularly of dark keratin fibres, towards lighter shades, by modifying the shade of these fibres where appropriate, constitutes a major demand.

Conventionally, in order to obtain a lighter dyeing, a chemical bleaching method is employed. This method involves treating the keratin materials such as the keratin fibres, more particularly the hair, with a strong oxidizing system, generally composed of hydrogen peroxide, combined or not with persalts, typically in an alkaline medium.

This bleaching system has the drawback of degrading the fibres and impairing their cosmetic properties. Specifically, the fibres tend to become coarse, more difficult to disentangle and more fragile. Finally, the lightening or bleaching of keratin fibres on the basis of an oxidizing agent is incompatible with treatments for modifying the shape of said fibres, particularly in straightening treatments.

Another lightening technique involves applying fluorescent direct dyes to dark hair. This technique, described more particularly in the document FR 2830189, allows the quality of the keratin fibre to be respected in the course of the treatment; however, the fluorescent dyes that are employed are not satisfactorily resistant to shampooing.

In order to enhance the persistence of direct dyeings, the fixing of the direct dyes to the hair by covalent bonding is known. It is known for example, to react dyes containing reactive groups with the cystine or cysteine residues which are very numerous in keratin fibres. Hence certain dyes have been described that carry Bunte salt and isothiuronium functions or other thiol-protecting groups. However, obtaining the reactive form of the dye generally necessitates the use of strongly basic media. Moreover, the thiol functions are generally generated in excess, thereby necessitating a step of subsequent neutralization following dyeing.

Other disulphide dyes known for the dyeing of keratin fibres are disulphide derivatives of aminothiophenol derivatives. Such dyes are described, for example, in patent FR 1156407. These dyes may be used under relatively gentle conditions, in the presence of a slightly reducing medium or after a reducing pretreatment on the hair. These dyes, however, may give rise to unwanted colour changes on application.

Finally, the document WO 2005/097051 describes azaimidazolium disulphide dyes for the direct dyeing of keratin fibres.

The aim of the present invention is to provide new systems for dyeing keratin materials with a lightening effect, especially human keratin fibres, particularly the hair, that do not have the drawbacks of the existing bleaching methods. More particularly, one of the aims of the present invention is to provide systems for direct colouring that allow lightening effects to be obtained more particularly on naturally or artificially dark keratin fibres, these effects being persistent in response to successive shampooings, without detriment to the keratin fibres and without impairing their cosmetic properties.

This aim is achieved with the present invention, which provides a method of colouring dark keratin materials that involves applying to the keratin materials a dyeing composition comprising in an appropriate cosmetic medium at least one fluorescent disulphide dye for example selected from the dyes of formulae (I) and (II) below:

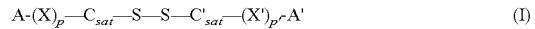

$$A\text{-}(X)_p\text{—}C_{sat}\text{—}S\text{—}S\text{—}C'_{sat}\text{—}(X')_{p'}\text{-}A' \quad (I)$$

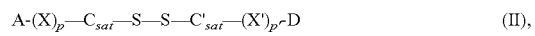

$$A\text{-}(X)_p\text{—}C_{sat}\text{—}S\text{—}S\text{—}C'_{sat}\text{—}(X')_{p'}\text{-}D \quad (II),$$

their organic or inorganic acid salts, optical isomers, geometrical isomers, and the solvates such as hydrates, in which formulae:

A and A', which are identical or different, each represent a radical containing at least one cationic or non-cationic fluorescent chromophore;

X and X', which are identical or different, each represent a saturated or unsaturated, linear or branched $C_1$-$C_{30}$ hydrocarbon chain which is optionally interrupted and/or optionally terminated at one or two of its ends by one or more divalent groups or combinations thereof selected from:

—N(R)—, —N⁺(R)(R')—, —O—, —S—, —CO—, —SO₂— where R and R', which are identical or different, are each selected from a hydrogen or a $C_1$-$C_4$ alkyl, hydroxyalkyl or aminoalkyl radical;

a saturated or unsaturated, fused or non-fused, aromatic or non-aromatic (hetero)cyclic radical optionally comprising one or more identical or non-identical heteroatoms and optionally substituted;

the coefficients p and p', which are identical or different, each represent an integer equal to 0 or 1;

$C_{sat}$ and $C'_{sat}$, which are identical or different, each represent an optionally cyclic, optionally substituted, linear or branched $C_1$-$C_{18}$ alkylene chain;

D corresponds to a radical selected from hydroxyl, hydroxyalkyl, alkoxy, carboxyl, carboxylate, amino, alkylamino and dialkylamino radicals; this application is performed in the presence of a reducing agent.

This reducing agent may be selected from thiols, for example cysteine, homocysteine, thiolactic acid, the salts of these thiols, phosphines, bisulphite, sulphites, thioglycolic acid, and also its esters, particularly glycerol monothioglycolate, and thioglycerol.

This reducing agent may also be selected from borohydrides and their derivatives, such as, for example, borohydride, cyanoborohydride, triacetoxyborohydride and trimethoxyborohydride salts: sodium, lithium, potassium, calcium, quaternary ammonium (tetramethylammonium, tetraethylammonium, tetra-n-butylammonium and benzyltriethylammonium) salts; and catecholborane.

The method of the invention allows lightening of dark keratin materials to be obtained. In particular the method of the invention allows keratin fibres such as the hair to be lightened in a way which is very persistent in response to shampooing, to common harsh influences (sun, perspiration) and to other hair treatments, without degrading the keratin fibre.

For the purposes of the invention a dark keratin material is one which exhibits a lightness L* in the C.I.E. L*a*b* system of less than or equal to 45 and preferably less than or equal to 40, where an L* of 0 corresponds to black and an L* of 100 to white.

For the purposes of the invention, hair which is naturally or artificially dark is hair whose tone level is less than or equal to 6 (dark blond) and preferably less than or equal to 4 (brown).

The lightening of the hair is evaluated via the "tone level", which characterizes the degree or level of lightening. The "tone" concept is based on the classification of natural shades, with one tone separating each shade from its immediate precursor or successor. This definition, and the classification of the natural shades, is well known to haircare professionals and is published in the work "Science des traitements capillaires" by Charles ZVIAK, Masson, 1988, pages 215 and 278.

The tone levels range from 1 (black) to 10 (light light blond), one unit corresponding to one tone; the higher the number the lighter the shade.

Artificially coloured hair is hair whose colour has been modified by a dyeing treatment, for example dyeing with direct dyes or oxidation dyes.

Preferably, following application to hair, brown hair for example, the composition must lead to the results below.

The parameter of interest is the reflectance performances of the hair when irradiated with visible light in the wavelength range from 400 to 700 nanometres.

The curves of reflectance as a function of wavelength are then compared for hair treated with the composition of the invention and untreated hair.

The curve corresponding to the treated hair is required to show a reflectance in the wavelength range from 450 to 700 nanometres which is greater than the curve corresponding to the untreated hair.

This means that, in the wavelength range from 450 to 700 nanometres, there is at least one range in which the reflectance curve corresponding to the treated hair is higher than the reflectance curve corresponding to the untreated hair. By "higher" is meant a difference of at least 0.05% reflectance, and preferably at least 0.1%. This is not to rule out the possibility that, within the wavelength range from 450 to 700 nanometres, there is at least one range in which the reflectance curve corresponding to the treated hair is either superimposable on or lower than the reflectance curve corresponding to the untreated hair.

The wavelength of maximum difference between the reflectance curve of the treated hair and that of the untreated hair is preferably situated within the wavelength range from 450 to 650 nanometres, and preferably in the wavelength range from 450 to 620 nanometres.

For the purposes of the present invention, and in the absence of any indication to the contrary:

a fluorescent disulphide dye is a fluorescent compound containing at least one fluorescent chromophore as defined hereinafter and containing one or more S—S disulphide bonds between two carbon atoms which are connected directly or indirectly to the fluorescent chromophore(s) of the compound; preferably the bond is capable of being reduced in a cosmetically acceptable medium;

the "aryl" or "heteroaryl" radicals or the aryl or heteroaryl moiety of a radical may be substituted by at least one substituent carried by a carbon atom and selected from:

a $C_1$-$C_{16}$, preferably $C_1$-$C_8$, alkyl radical which is optionally substituted by one or more radicals selected from the following radicals: hydroxyl, $C_1$-$C_2$ alkoxy, $C_2$-$C_4$ (poly)-hydroxyalkoxy, acylamino, amino substituted by two, identical or different, $C_1$-$C_4$ alkyl radicals which optionally carry at least one hydroxyl group, it being possible for the two radicals to form, with the nitrogen atom to which they are attached, a heterocycle containing 5 to 7 members, preferably 5 or 6 members, which is saturated or unsaturated and optionally substituted and optionally comprises another heteroatom identical to or different from the nitrogen;

a halogen atom such as chlorine, fluorine or bromine;

a hydroxyl group;

a $C_1$-$C_2$ alkoxy radical; a $C_2$-$C_4$ (poly)-hydroxyalkoxy radical;

an amino radical;

a 5- or 6-membered heterocycloalkyl radical;

a 5- or 6-membered heteroaryl radical which is optionally cationic, preferably imidazolium, and is optionally substituted by a ($C_1$-$C_4$)alkyl radical, preferably methyl;

an amino radical substituted by one or two identical or different $C_1$-$C_6$ alkyl radicals which optionally carry at least:

i) a hydroxyl group, ii) an amino group which is optionally substituted by one or two, optionally substituted $C_1$-$C_3$ alkyl radicals, it being possible for said alkyl radicals to form, with the nitrogen atom to which they are attached, a heterocycle containing 5 to 7 members which is saturated or unsaturated, optionally substituted and optionally comprises at least one other heteroatom different or not from nitrogen, iii) a quaternary ammonium group —N$^+$R'R"R'", M$^-$ for which R', R" and R'", which are identical or different, each represent a hydrogen atom or a $C_1$-$C_4$ alkyl group; and M$^-$ represents the counterion of the corresponding halide or organic or inorganic acid, iv) or a 5- or 6-membered heteroaryl radical which is optionally cationic, preferably imidazolium, and is optionally substituted by a ($C_1$-$C_4$)alkyl radical, preferably methyl;

an acylamino radical (—NR—COR') in which the radical R is a hydrogen atom or a $C_1$-$C_4$ alkyl radical which optionally carries at least one hydroxyl group and the radical R' is a $C_1$-$C_2$ alkyl radical; a carbamoyl radical ((R)$_2$N—CO—) in which the radicals R, which are identical or not, each represent a hydrogen atom or a $C_1$-$C_4$ alkyl radical which optionally carries at least one hydroxyl group; an alkylsulphonylamino radical (R'SO$_2$—NR—) in which the radical R represents a hydrogen atom or a C$_1$-C$_4$ alkyl radical which optionally carries at least one hydroxyl group, and the radical R' represents a C$_1$-C$_4$ alkyl radical or a phenyl radical; an aminosulphonyl radical ((R)$_2$N—SO$_2$—) in which the radicals R, which are identical or not, each represent a hydrogen atom or a C$_1$-C$_4$ alkyl radical which optionally carries at least one hydroxyl group, a carboxyl radical in acid form or salified form (preferably with an alkali metal or a substituted or unsubstituted ammonium);

a cyano group (CN);

a polyhaloalkyl group, preferably trifluoromethyl (CF$_3$);

the cyclic or heterocyclic moiety of a non-aromatic radical may be substituted by at least one substituent carried by a carbon atom and selected from the following groups: hydroxyl, C$_1$-C$_4$ alkoxy, C$_2$-C$_4$ (poly)hydroxyalkoxy, alkylcarbonylamino ((RCO—NR'—) in which the radical R' is a hydrogen atom or a C$_1$-C$_4$ alkyl radical which optionally carries at least one hydroxyl group, and the radical R is a C$_1$-C$_2$ alkyl radical, amino substituted by two identical or different C$_1$-C$_4$ alkyl groups which optionally carry at least one hydroxyl group, it being possible for said alkyl radicals to form, with the nitrogen atom to which they are attached, a heterocycle containing 5 to 7 members which is saturated or unsaturated, is optionally substituted and optionally comprises at least one other heteroatom, different or not from nitrogen;

alkylcarbonyloxy ((RCO—O—) in which the radical R is a C$_1$-C$_4$ alkyl radical, amino substituted by two identical or different C$_1$-C$_4$ alkyl groups which optionally carry at least one hydroxyl group, it being possible for said alkyl radicals to form, with the nitrogen atom to which they are attached, a heterocycle containing 5 to 7 members which is saturated or unsaturated, is optionally substituted and optionally comprises at least one other heteroatom, different or not from nitrogen;

alkoxycarbonyl ((RO—CO—) in which the radical R is a C$_1$-C$_4$ alkyl radical, amino substituted by two identical or different C$_1$-C$_4$ alkyl groups which optionally carry at least one hydroxyl group, it being possible for said alkyl radicals to form, with the nitrogen atom to which they are attached, a heterocycle containing 5 to 7 members which is saturated or unsaturated, is optionally substituted and optionally comprises at least one other heteroatom, different or not from nitrogen;

a cyclic or heterocyclic radical or a non-aromatic moiety of an aryl or heteroaryl radical may also be substituted by one or more oxo groups;

a hydrocarbon chain is unsaturated when it contains one or more double bonds and/or one or more triple bonds;

an "aryl" radical represents a fused or non-fused monocyclic or polycyclic group which contains 6 to 22 carbon atoms and includes at least one aromatic ring; preferably the aryl radical is a phenyl, biphenyl, naphthyl, indenyl, anthracenyl or tetrahydronaphthyl;

a "heteroaryl radical" represents a fused or non-fused, optionally cationic, monocyclic or polycyclic group containing 5 to 22 members, 1 to 6 heteroatoms selected from nitrogen, oxygen, sulphur and selenium atoms, and including at least one aromatic ring; preferably a heteroaryl radical is selected from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt;

a "cyclic radical" is a fused or non-fused, monocyclic or polycyclic, non-aromatic cycloalkyl radical containing 5 to 22 carbon atoms and able to contain from 1 to a plurality of unsaturations:

a "heterocyclic radical" is a fused or non-fused, monocyclic or polycyclic, non-aromatic radical containing 5 to 22 members and containing 1 to 6 heteroatoms selected from nitrogen, oxygen, sulphur and selenium atoms;

an "alkyl radical" is a linear or branched, C$_1$-C$_{16}$, preferably C$_1$-C$_8$ hydrocarbon radical;

the expression "optionally substituted" attributed to the alkyl radical means that said alkyl radical may be substituted by one or more radicals selected from the following radicals: i) hydroxyl, ii) C$_1$-C$_4$ alkoxy, iii) acylamino, iv) amino optionally substituted by one or two identical or different C$_1$-C$_4$ alkyl radicals, it being possible for said alkyl radicals to form, with the nitrogen atom which carries them, a heterocycle containing 5 to 7 members and optionally comprising another heteroatom which is different or not from nitrogen; v) or a quaternary ammonium group —N$^+$R'R"R''', M$^-$ for which R', R" and which are identical or different, each represent a hydrogen atom or a C$_1$-C$_4$ alkyl group, or —N$^+$R'R"R''' forms a heteroaryl such as imidazolium which is optionally substituted by a C$_1$-C$_4$ alkyl group, and M$^-$ represents the counterion of the corresponding halide, organic or inorganic acid;

an "alkoxy radical" is an alkyl-oxy radical for which the alkyl radical is a C$_1$-C$_{16}$, preferably C$_1$-C$_8$, linear or branched hydrocarbon radical;

when the alkoxy group is optionally substituted, this means that the alkyl group is optionally substituted as defined above.

Moreover, unless indicated otherwise, the top and bottom values delimiting the extent of a range of values are included within said range of values.

According to the present invention a "fluorescent chromophore" is a radical obtained from a fluorescent compound. A fluorescent compound is a compound which is capable of absorbing UV or visible radiation at a wavelength $\lambda_{abs}$ between 250 and 800 nm and capable of re-emitting in the visible range at an emission wavelength $\lambda_{em}$ of between 400 and 800 nm.

The fluorescent compounds are preferably dyes which are capable of absorbing $\lambda_{abs}$ between 400 and 800 nm in the visible and of re-emitting $\lambda_{em}$ between 400 and 800 nm in the visible. More preferably the fluorescent dyes are dyes which are capable of absorbing at a $\lambda_{abs}$ of between 420 nm and 550 nm and of re-emitting in the visible at a $\lambda_{em}$ of between 470 and 600 nm.

I. Dyes of Formulae (I) and (II)

The radicals A and A' of the formulae (I) and (II) may contain one or more identical or different fluorescent chromophores.

I.1. Chromophores

For the purposes of the present invention the chromophores are said to be different when they differ in their chemical structure. Such chromophores may be chromophores obtained from different classes or from a single class but having different chemical structures. For example, the chromophores may be selected from the class of the (poly)methine dyes but may differ in the chemical structure of the radicals constituting them or in the respective position of these radicals.

Fluorescent chromophores which are useful in the present invention include the radicals obtained from acridine, acridone, benzanthrone, benzimidazole, benzimidazolone, benzindole, benzoxazole, benzopyran, benzothiazole, coumarin, difluoro{2-[(2H-pyrrol-2-ylidene-kN)methyl]-1H-pyrrolato-kN}boron (BODIPY®), dipyrrinone, diketopyrrolopyrrole, fluorindine, (poly)methine (particularly cyanine and styryl/hemicyanine), naphthalimide, naphthanilide, naphthylamine (such as the dansyls), oxadiazole, oxazine, perilone, perinone, perylene, polyene/carotenoid, squarane, stilbene and xanthene dyes.

Mention may also be made of the fluorescent dyes that are described in the documents EP 1133975, WO 03/029359, EP 860636, WO 95/01772, WO 95/15144 and EP 714954, and those listed in the encyclopaedia "*The chemistry of synthetic dyes*" by K. VENKATARAMAN, 1952, Academic Press, Volumes 1 to 7, in the encyclopaedia "*Kirk Othmer*" Chemical technology, "Dyes and dye intermediates" chapter, 1993, Wiley and Sons, and in various chapters of the encyclopaedia "ULLMANN's ENCYCLOPEDIA of Industrial Chemistry", 7th Edition, Wiley and Sons, and in *The Handbook—A Guide to Fluorescent Probes and Labeling Technologies,* 10th Edition, Molecular Probes/Invitrogen—Oregon 2005, distributed on the Internet or in the previous printed editions.

Preferably the chromophores are selected from those obtained from dyes of coumarin, (poly)methine (more particularly cyanine and styryl/hemicyanine) and naphthalimide types.

In one variant the radicals A and A' of the formulae (I) or (II) contain at least one cationic radical which is carried by or included in at least one of the chromophores.

Preferably the cationic radical is a quaternary ammonium.

These cationic radicals are, for example, an alkylammonium, acridinium, benzimidazolium, benzobistriazolium, benzopyrazolium, benzopyridazinium, benzoquinolium, benzothiazolium, benzotriazolium, benzoxazolium, bipyridinium, bistetrazolium, dihydrothiazolium, imidazopyridinium, imidazolium, indolium, isoquinolium, naphthoimidazolium, naphthooxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium radical.

I.2. $C_{sat}$ and $C'_{sat}$:

As indicated previously, in the formulae (I) or (II), $C_{sat}$ and $C'_{sat}$, independently of one another, represent an optionally cyclic, optionally substituted, linear or branched $C_1$-$C_{18}$ alkylene chain. Substituents include amino ($C_1$-$C_4$)alkylamino or ($C_1$-$C_4$)dialkylamino groups or the group $R^a$—$Z^a$—$C(Z^b)$— (in which $Z^a$ and $Z^b$, which are identical or different, each represent an oxygen or sulphur atom or a group $NR^{a'}$, and $R^a$ represents an alkali metal, a hydrogen atom or a $C_1$-$C_4$ alkyl group and $R^{a'}$ represents a hydrogen atom or a $C_1$-$C_4$ alkyl group), which are present preferably on the carbon in the position beta or gamma to the sulphur atoms.

Preferably, in the case of the formulae (I) or (II), $C_{sat}$ and $C'_{sat}$ represent a chain —$(CH_2)_k$— where k is an integer of between 1 and 8 inclusive.

I.3. X and X':

In accordance with one particular embodiment of the invention, in the formulae (I) or (II) above, when p is 1, X and X', which are identical or different, each represent the following sequence:

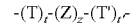

said sequence being connected in the formulae (I) or (II) symmetrically as follows:

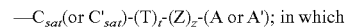

T and T', which are identical or different, each represent one or more radicals or combinations thereof selected from the following: —$SO_2$—; —O—; —S—; —N(R)—; —$N^+(R)(R^o)$—; —CO—; where R and $R^o$, which are identical or different, each represent a hydrogen atom or a $C_1$-$C_4$ alkyl, $C_1$-$C_4$ hydroxyalkyl or aryl($C_1$-$C_4$)alkyl radical; and a preferably monocyclic, cationic or non-cationic, heteroaryl or heterocycloalkyl radical containing preferably two heteroatoms (more preferably two nitrogen atoms) and containing preferably 5 to 7 members, more preferably imidazolium;

the indices t and t', which are identical or different, are each 0 or 1.

Z represents:

—$(CH_2)_m$— where m is an integer between 1 and 8
$(CH_2CH_2O)_q$— or —$(OCH_2CH_2)_q$— in which q is an integer between 1 and an aryl, alkylaryl or arylalkyl radical in which the alkyl radical is $C_1$-$C_4$ and the aryl radical is preferably $C_6$, this radical being optionally substituted by at least one group $SO_3M$ where M represents a hydrogen atom, an alkali metal or an ammonium group substituted by one or more identical or non-identical, linear or branched, $C_1$-$C_{18}$ alkyl radicals which optionally carry at least one hydroxyl z is 0 or 1.

Furthermore, according to one particular embodiment of the invention, Z represents:

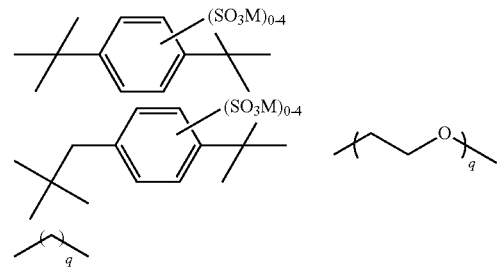

I.4. Fluorescent Disulphide Dyes:

In one preferred variant of the invention the disulphide dye is a cationic fluorescent dye comprising at least one quaternary ammonium radical and being such that, in the formula (I) with p being 1:

A and A', which are identical or different, more preferably identical, each represent W—$C(R^c)$=$C(R^d)$—Ar— or —W—$C(R^c)$=$C(R^d)$—Ar, where W represents a heterocycle or a heteroaryl containing a quaternary ammonium; Ar represents a 5- or 6-membered (hetero)aryl radical of phenyl or pyridinium type, or a (hetero)aromatic bicyclic system of naphthyl, benzopyridinium, indolinyl or benzoindolinyl type, which are optionally substituted by one or more halogen atoms, preferably chlorine, fluorine; by one or more alkyl groups, preferably $C_1$-$C_4$ alkyl groups; by one or more hydroxyl groups; by one or more alkoxy groups, by one or more hydroxyalkyl groups, by one or more amino or (di)alkylamino groups, preferably with the alkyl moiety being $C_1$-$C_4$, by one or more acylamino groups; by one or more 5- or 6-membered heteroaryl or heterocycloalkyl groups selected preferably from pyrrolidinyl, piperazinyl, piperidinyl and imidazolinyl; 13' and $R^d$, which are identical or different, each represent a hydrogen atom or a $C_1$-$C_4$ alkyl group.

In one preferred variant p, p'=1; z=0; t'=0 and t=1, and T represents —N(R)—, preferably in the para position on Ar relative to the olefin function —C($R^c$)=C($R^d$)—.

In another preferred variant p, p'=1; z=0; t, t'=1; T represents —N(R)—, preferably in the para position on Ar relative to the olefin function —C($R^c$)=C($R^d$)— and T' represents a group —N(R)—, —$N^+$(R)($R^o$) or an imidazolium.

Preferably W is an imidazolium, pyridinium, benzopyridinium, benzimidazolium, quinolinium and pyrazolium which are optionally substituted by one or more identical or non-identical $C_1$-$C_4$ alkyl radicals.

In another preferred variant the disulphide dye is a cationic fluorescent dye containing at least one quaternary ammonium radical and such that, in the formula (I) with p being 1:

A represents a naphthalimidyl radical of the formula:

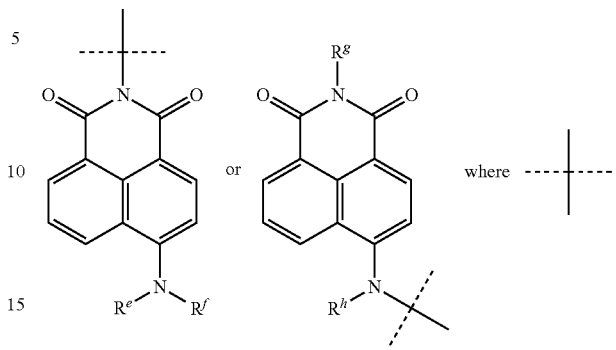

represents the bond with the group X or X', $C_{sat}$ or $C'_{sat}$, wherein $R^e$, $R^f$, $R^g$ and $R^h$, which are identical or different, each represent a hydrogen atom or an optionally substituted $C_1$-$C_6$ alkyl group.

More preferably the disulphide dye is a fluorescent dye selected from:

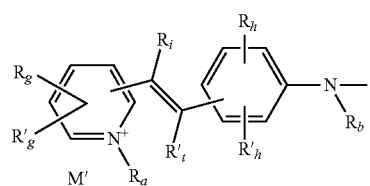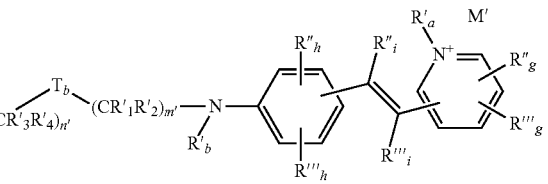

(III)

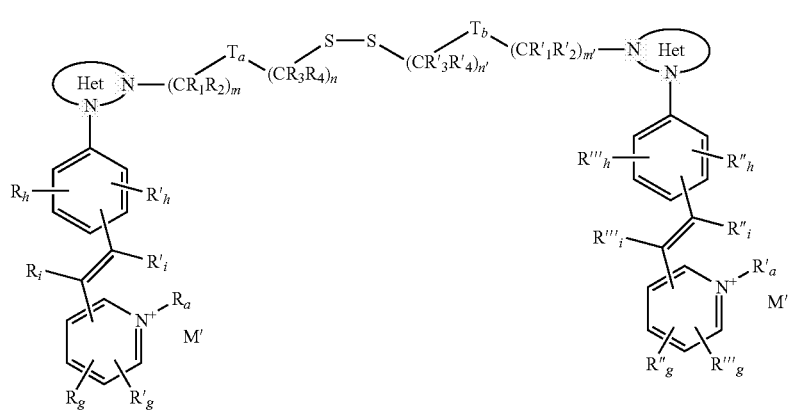

(IV)

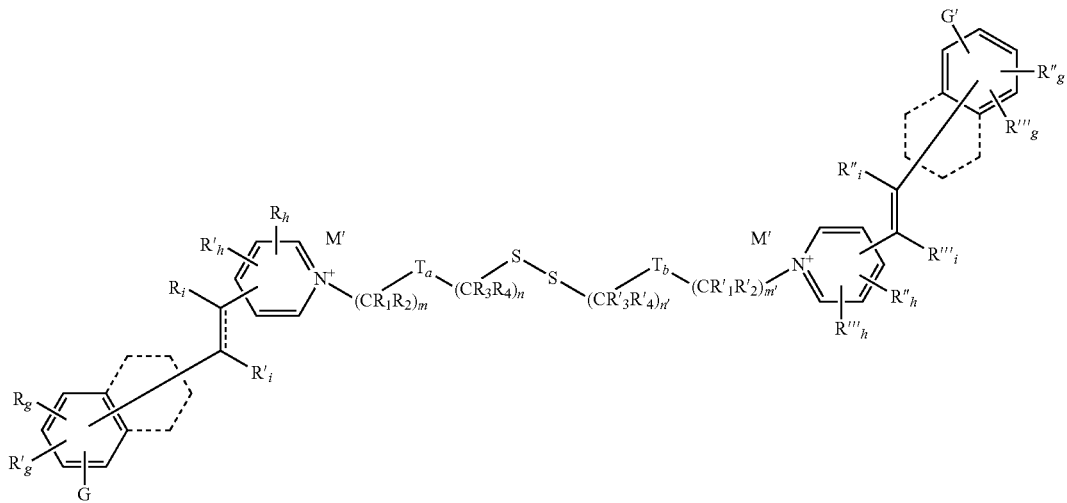
(V)
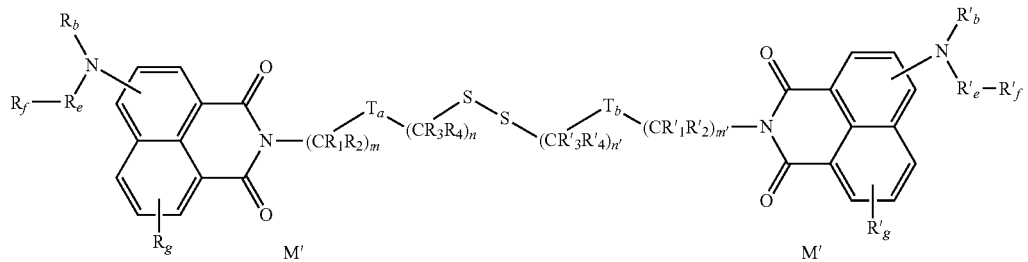
(VI)
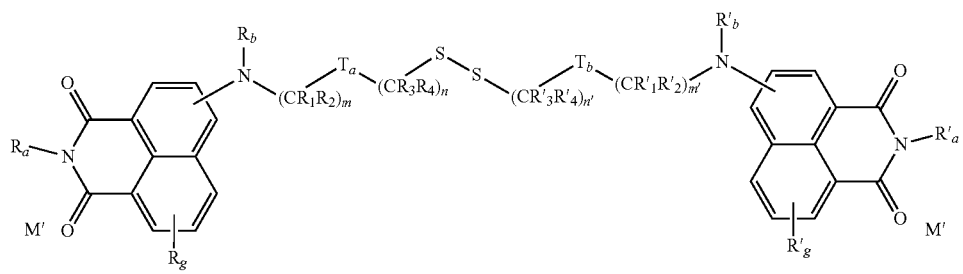
(VII)
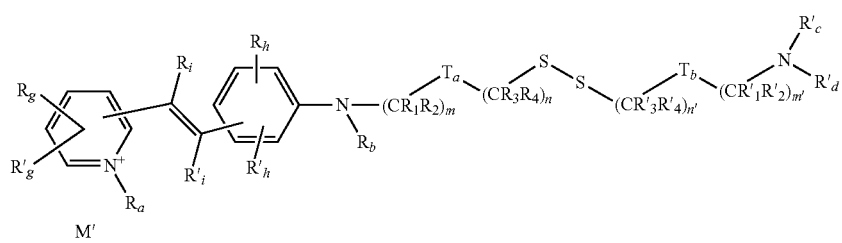
(VIII)

-continued

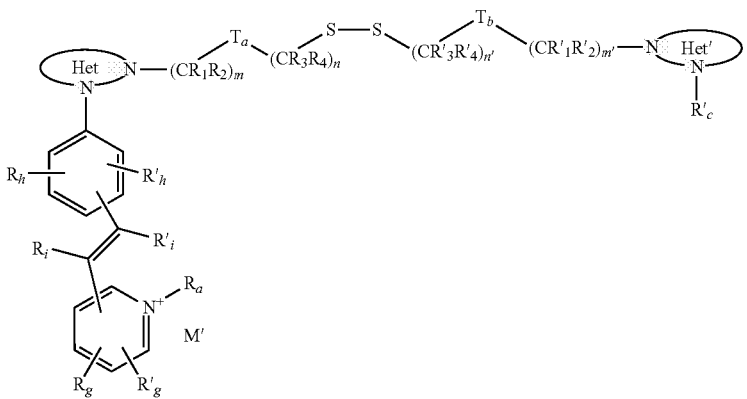
(IX)

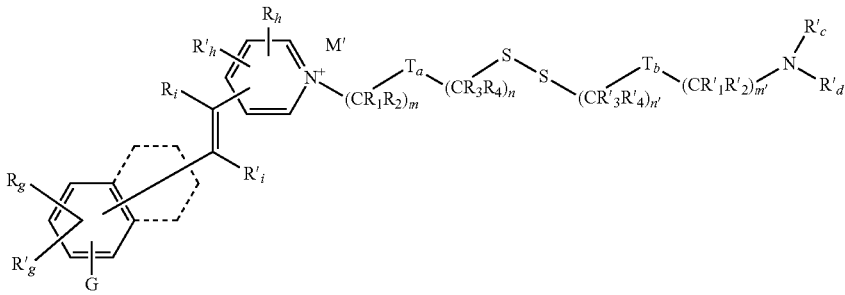
(X)

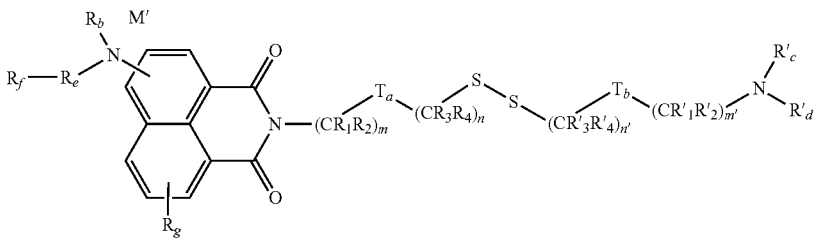
(XI)

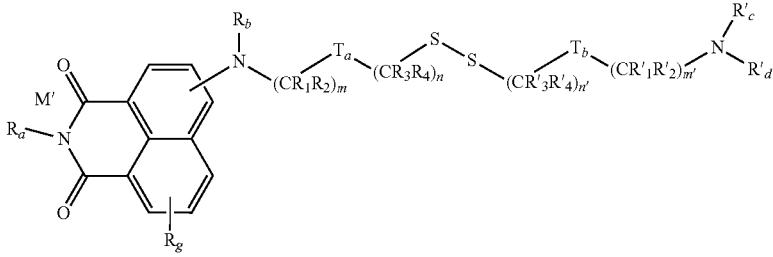
(XII)

in which
G and G', which are identical or different, each represent a group —$NR_cR_d$, —$NR'_cR'_d$ or optionally substituted, preferably unsubstituted, $C_1$-$C_6$ alkoxy; preferably G and G' represent respectively a group —$NR_cR_d$ and $R_a$ and $R'_a$, which are identical or different, represent an aryl($C_1$-$C_4$)alkyl group or a $C_1$-$C_6$ alkyl group which is optionally substituted by a hydroxyl or amino group, $C_1$-$C_4$ alkylamino or $C_1$-$C_4$ dialkylamino, it being possible for said alkyl radicals to form, with the nitrogen atom which carries them, a heterocycle containing from 5 to 7 chain members, optionally comprising another heteroatom different or not different from nitrogen; preferably $R_a$ and $R'_a$ represent a $C_1$-$C_3$ alkyl group which is optionally substituted by a hydroxyl group, or a benzyl group;

$R_b$ and $R'_b$, which are identical or different, each represent a hydrogen atom, an aryl($C_1$-$C_4$)alkyl group or a $C_1$-$C_6$ alkyl group which is optionally substituted; preferably $R_b$ and $R'_b$ each represent a hydrogen atom or a $C_1$-$C_3$ alkyl or benzyl group;

$R_c$, $R'_c$, $R_d$ and $R'_d$, which are identical or different, each represent a hydrogen atom, an aryl($C_1$-$C_4$)alkyl group, $C_1$-$C_6$ alkoxy or a $C_1$-$C_6$ alkyl group which is optionally substituted; $R_g$, $R'_c$, $R_d$ and $R'_d$ each represent preferably a hydrogen atom, a hydroxyl, $C_1$-$C_3$ alkoxy, amino or C₁-C₃ (di)alkylamino group or a C₁-C₃ alkyl group which is optionally substituted by i) a hydroxyl group, ii) amino, iii) C₁-C₃ (di)alkylamino, or iv) quaternary ammonium $(R''')(R'''')(R''''')N^+$; or two adjacent radicals $R_c$ and $R_d$ or $R'_c$ and $R'_d$ which are carried by the same nitrogen atom together form a heterocyclic or heteroaryl group; preferably the heterocycle or heteroaryl is monocyclic and contains between 5 and 7 members; more preferably the groups are selected from imidazolyl and pyrrolidinyl;

$R_e$ and $R'_e$, which are identical or different, each represent a divalent, linear or branched, optionally unsaturated C₁-C₆ alkylenyl hydrocarbon chain;

$R_f$ and $R'_f$ which are identical or different, each represent a quaternary ammonium group $(R'')(R''')(R'''')N^+$— where R", R''' and R'''', which are identical or different, each represent a hydrogen atom or a C₁-C₄ alkyl group, or $(R'')(R''')(R'''')^+$— represents an optionally substituted cationic heteroaryl group, preferably an imidazolinium group which is optionally substituted by a C₁-C₃ alkyl group;

$R_g$, $R'_g$, $R''_g$, $R'''_g$, $R_h$, $R'_h$, $R''_h$ and $R'''_h$, which are identical or different, each represent a hydrogen atom, a halogen atom, an amino, C₁-C₄ alkylamino, C₁-C₄ dialkylamino, cyano, carboxyl, hydroxyl or trifluoromethyl group, an acylamino, C₁-C₄ alkoxy, C₂-C₄ (poly)hydroxyalkoxy, alkylcarbonyloxy, alkoxycarbonyl or alkylcarbonylamino radical, an acylamino, carbamoyl or alkylsulphonylamino radical, an aminosulphonyl radical, or a C₁-C₁₆ alkyl radical optionally substituted by a group selected from C₁-C₁₂ alkoxy, hydroxyl, cyano, carboxyl, amino, C₁-C₄ alkylamino and C₁-C₄ dialkylamino, or the two alkyl radicals carried by the nitrogen atom of the amino group form a heterocycle containing 5 to 7 members and optionally comprising another heteroatom which is identical to or different from that of the nitrogen atom; preferably $R_g$, $R'_g$, $R''_g$, $R'''_g$, $R_h$, $R'_h$, $R''_h$ and $R'''_h$ represent a hydrogen or halogen atom or a C₁-C₃ alkyl group;

or two groups $R_g$ and $R'_g$; $R''_g$ and $R'''_g$; $R_h$ and $R'_h$; or $R''_h$ and $R'''_h$, carried by two adjacent carbon atoms, together form a benzo or indeno ring or a fused heteroaryl or fused heterocycloalkyl group, the benzo, indeno, heterocycloalkyl or heteroaryl ring being optionally substituted by a halogen atom, an amino, C₁-C₄ alkylamino, C₁-C₄ dialkylamino, nitro, cyano, carboxyl, hydroxyl or trifluoromethyl group, an acylamino, C₁-C₄ alkoxy, C₂-C₄ (poly)hydroxyalkoxy, alkylcarbonyloxy, alkoxycarbonyl, or alkylcarbonylamino radical, an acylamino, carbamoyl or alkylsulphonylamino radical, an aminosulphonyl radical, or a C₁-C₁₆ alkyl radical which is optionally substituted by a group selected from C₁-C₁₂ alkoxy, hydroxyl, cyano, carboxyl, amino, C₁-C₄ alkylamino or C₁-C₄ dialkylamino, or the two alkyl radicals carried by the nitrogen atom of the amino group form a heterocycle containing 5 to 7 members and optionally containing another heteroatom identical to or different from that of the nitrogen atom; preferably $R_g$ and $R'_g$, and $R''_g$ and $R'''_g$, together form a benzo group;

or, when G represents $-NR_cR_d$ and G' represents $-NR'_cR'_d$, two groups $R_c$ and $R'_g$; $R'_c$ and $R''_g$; $R_d$ and $R_g$; or $R'_d$ and $R'''_g$ together form a saturated heterocycle or heteroaryl which is optionally substituted by one or more C₁-C₆ alkyl groups, preferably a heterocycle containing one or two heteroatoms selected from nitrogen and oxygen and containing between 5 and 7 members; more preferably the heterocycle is selected from morpholinyl, piperazinyl, piperidinyl and pyrrolidinyl groups;

$R_i$, $R'_i$, $R''_i$, and $R'''_i$ which are identical or different, each represent a hydrogen atom or a C₁-C₄ alkyl group;

$R_1$, $R_2$, $R_3$, $R_4$, $R'_1$, $R'_2$, $R'_3$ and $R'_4$, which are identical or different, each represent a hydrogen atom or a C₁-C₄ alkyl, C₁-C₁₂ alkoxy, hydroxyl, cyano, carboxyl, amino, C₁-C₄ alkylamino or C₁-C₄ dialkylamino group, it being possible for said alkyl radicals to form, with the nitrogen atom which carries them, a heterocycle containing 5 to 7 members that optionally comprises another heteroatom which is different or not different from the nitrogen; preferably $R_1$, $R_2$, $R_3$, $R_4$, $R'_1$, $R'_2$, $R'_3$ and $R'_4$ are hydrogen atoms or an amino group; more preferably $R_1$, $R_2$, $R_3$, $R_4$, $R'_1$, $R'_2$, $R'_3$ and $R'_4$ represent a hydrogen atom;

$T_a$ and $T_b$, which are identical or different, represent i) a covalent σ bond, ii) one or more radicals or combinations thereof selected from $-SO_2-$, $-O-$, $-S-$, $-N(R)-$, $-N^+(R)(R°)-$, $-CO-$, with R and R°, which are identical or different, representing a hydrogen atom or a C₁-C₄ alkyl or C₁-C₄ hydroxyalkyl radical, or an aryl(C₁-C₄)alkyl; preferably $T_a$ is identical to $T_b$ and represents a covalent σ bond or a group selected from $-N(R)-$, $-C(O)-N(R)-$, $-N(R)-C(O)-$, $-O-C(O)-$, $-C(O)-O-$ and $-N^+(R)(R°)-$, where R and R°, which are identical or different, each represent a hydrogen atom or a C₁-C₄ alkyl group; more preferably $T_a$ and $T_b$ represent a σ bond; iii) or a cationic or non-cationic heteroaryl or heterocycloalkyl radical, which are preferably monocyclic, preferably identical, and containing preferably two heteroatoms (more preferably two nitrogen atoms) and containing preferably 5 to 7 members, such as imidazolium;

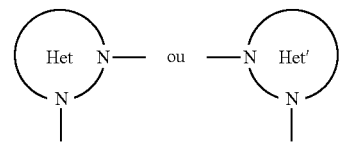

which are identical or different, each represent an optionally substituted heterocyclic group; preferably the heterocycles are identical, monocyclic and saturated and contain a total of two nitrogen atoms and 5 to 8 members;

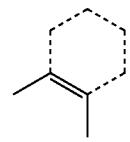

represents an aryl or heteroaryl group which is fused to the phenyl ring; or is absent from the phenyl ring; preferably, when the ring is present, the ring is a benzo;

m, m', n and n', which are identical or different, represent an integer of between 0 and 6 inclusive, with m+n and m'+n', which are identical or different, each representing an integer between 1 and 10 inclusive; preferably m+n=m'+n'=an integer between 2 and 4 inclusive; more preferably m+n=m'+n'=an integer equal to 2;

M' represents a counterion or an organic or inorganic acid salt.

Examples of fluorescent disulphide dyes include particularly the following compounds:
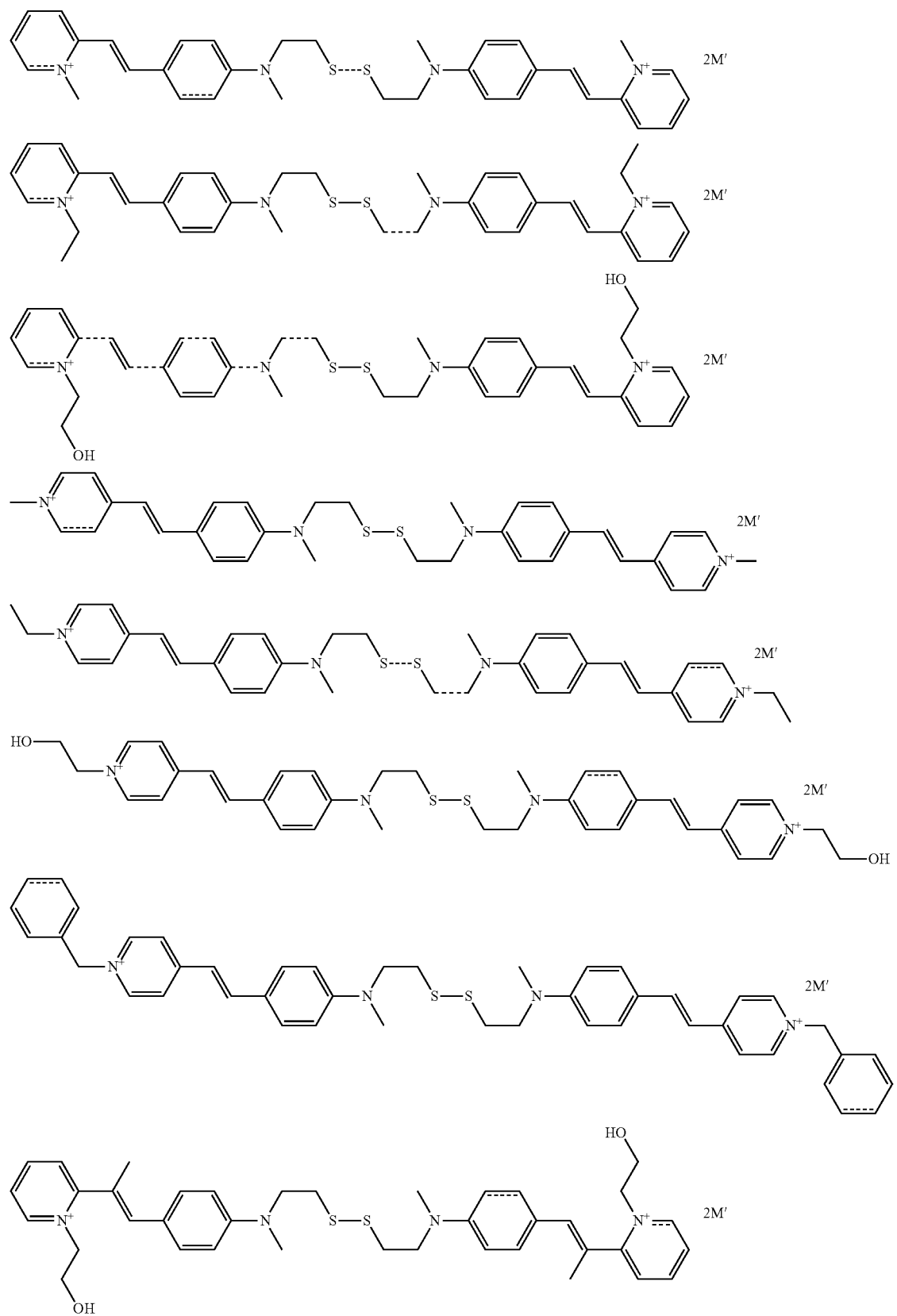

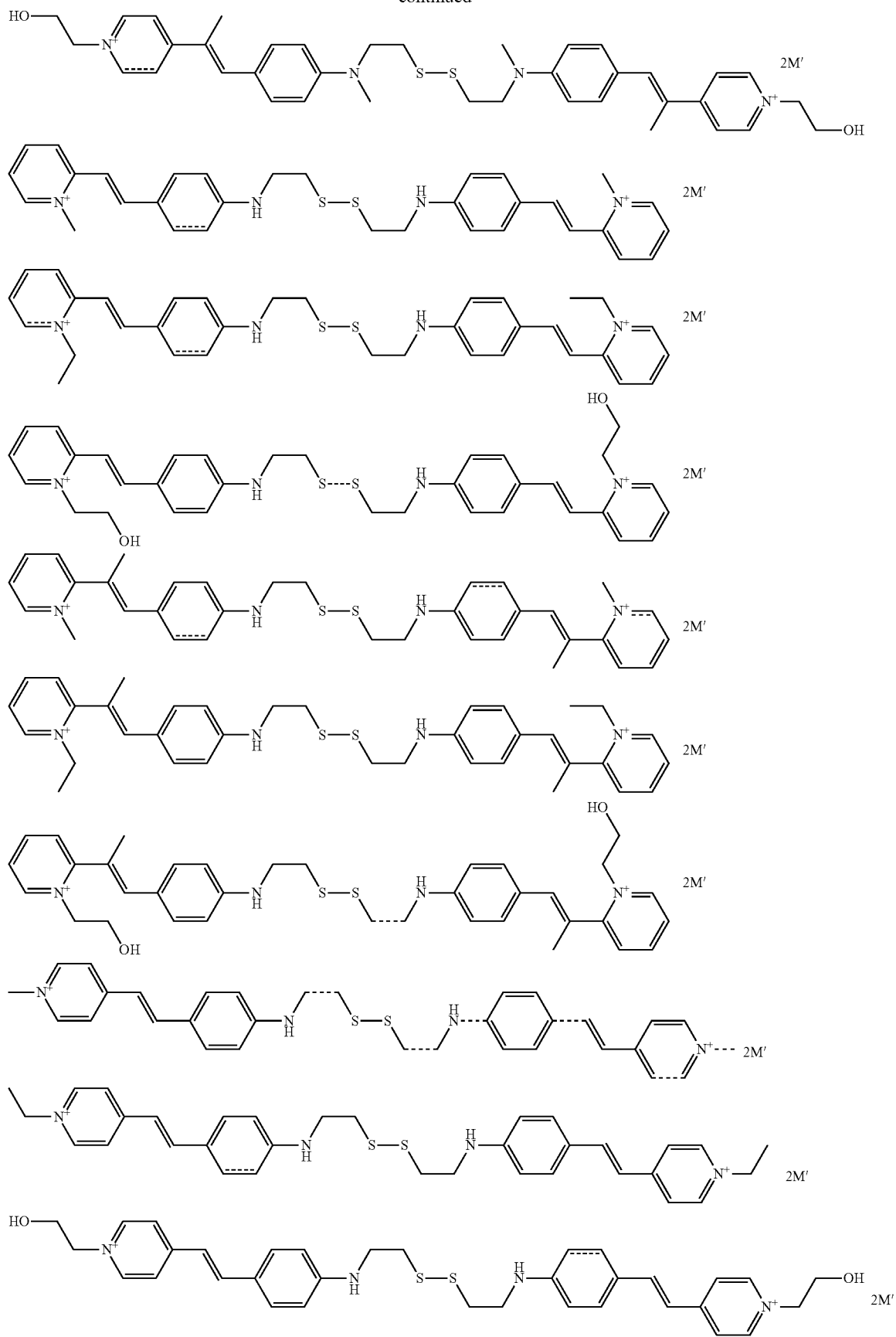

-continued
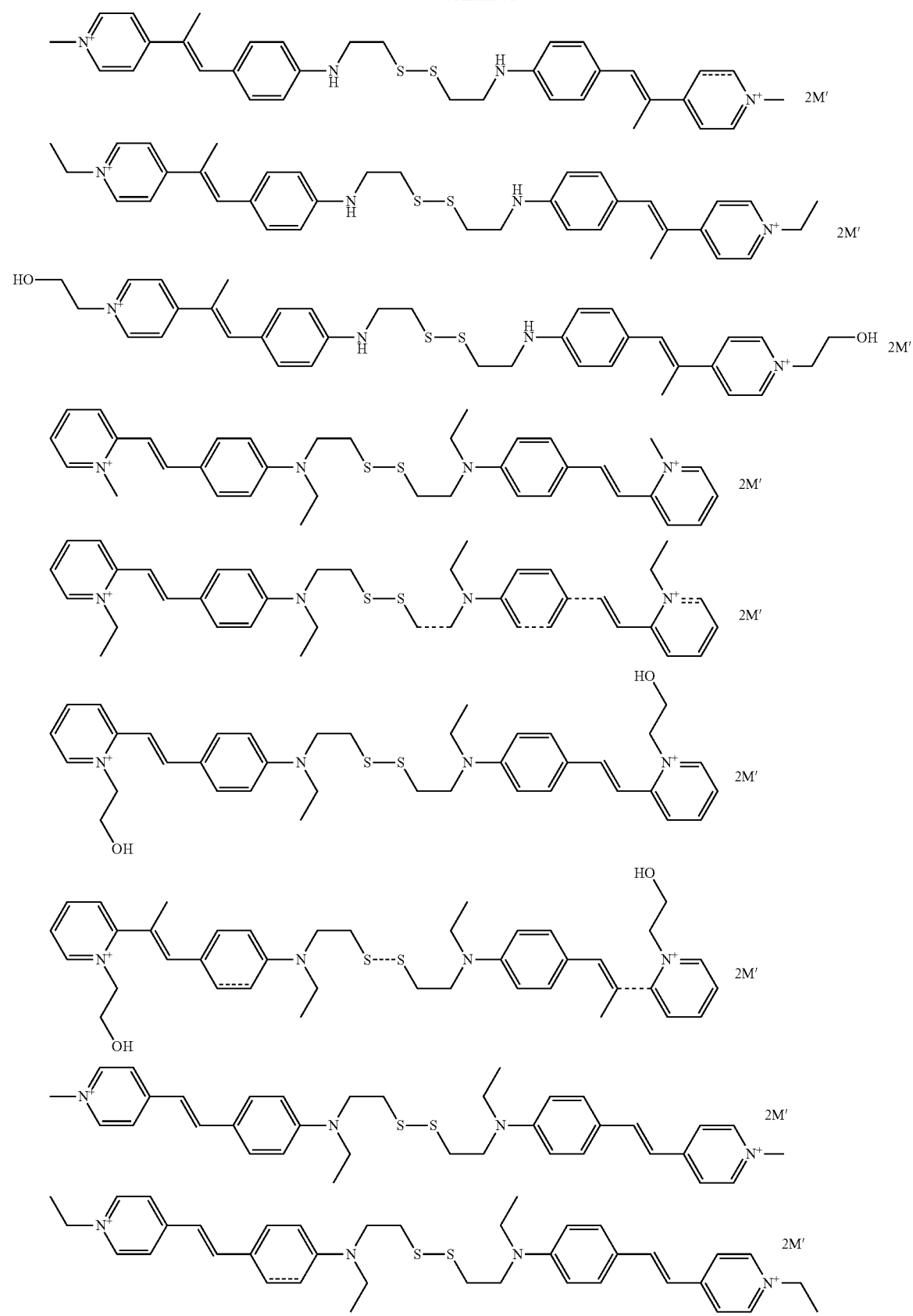

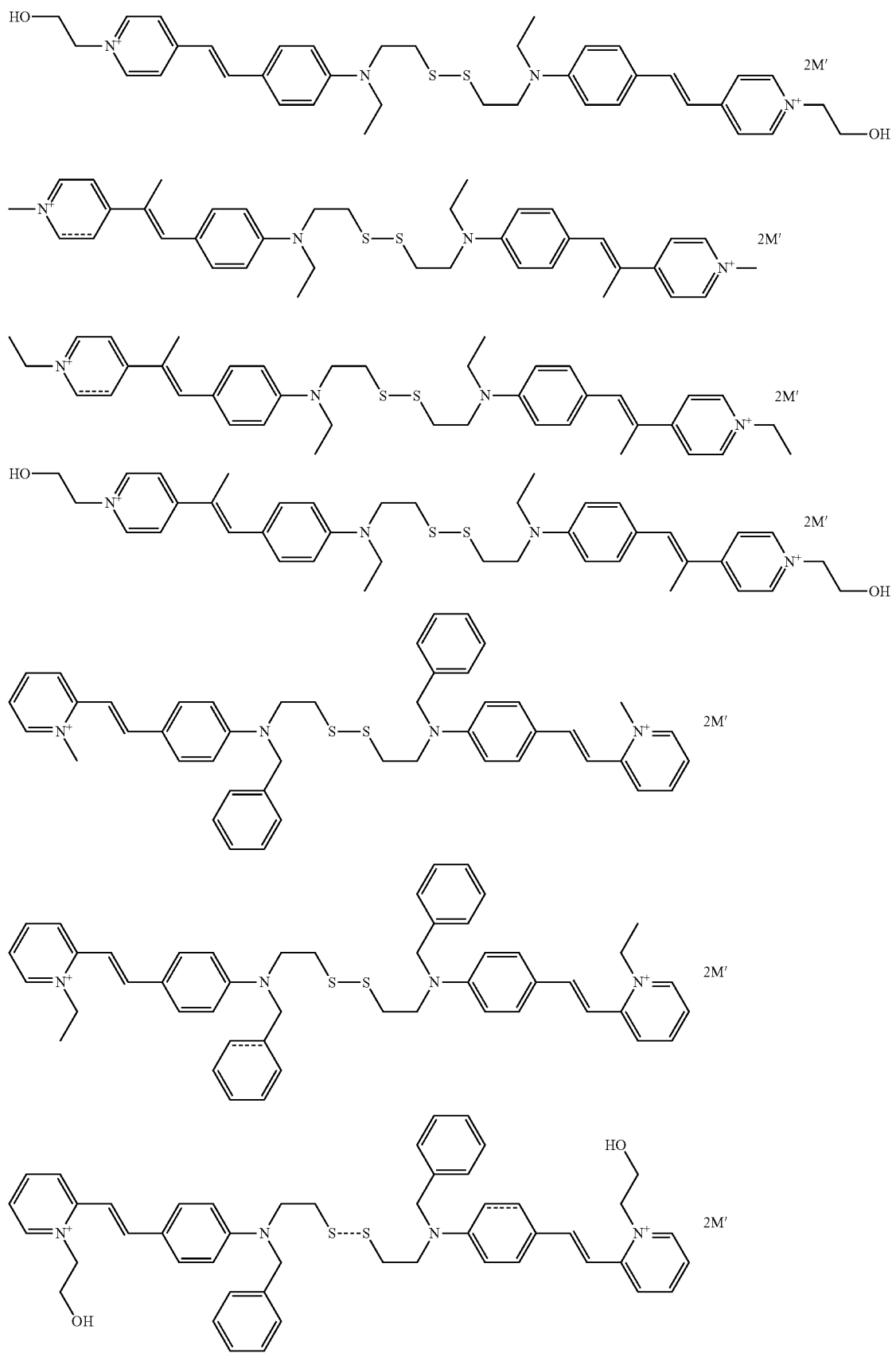

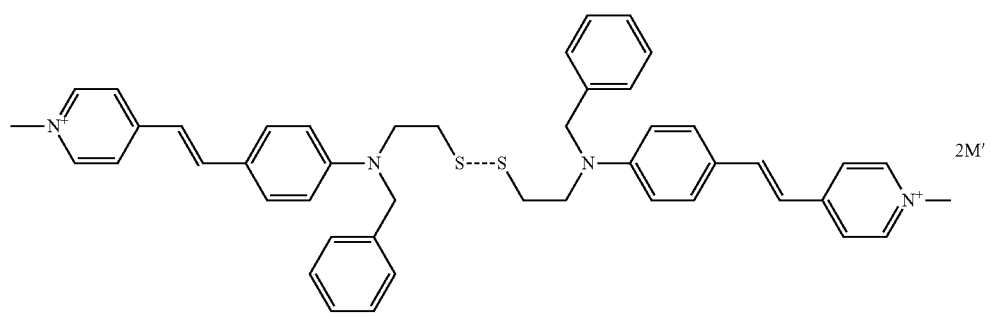
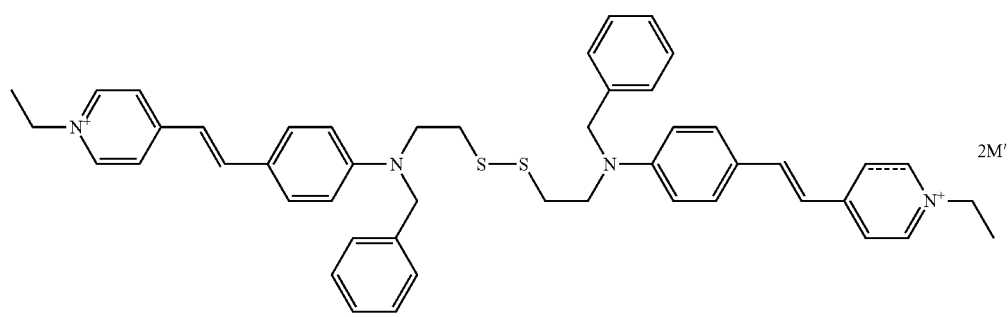
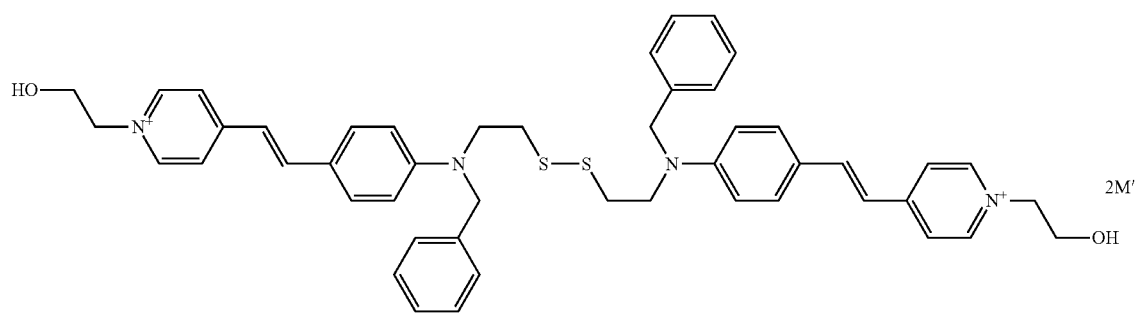
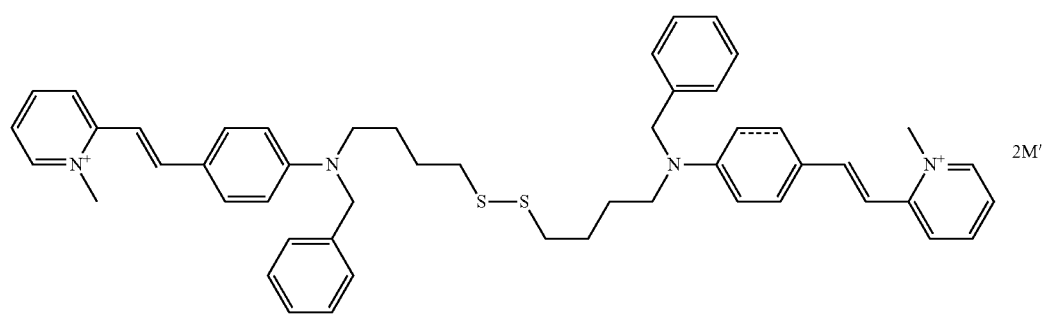
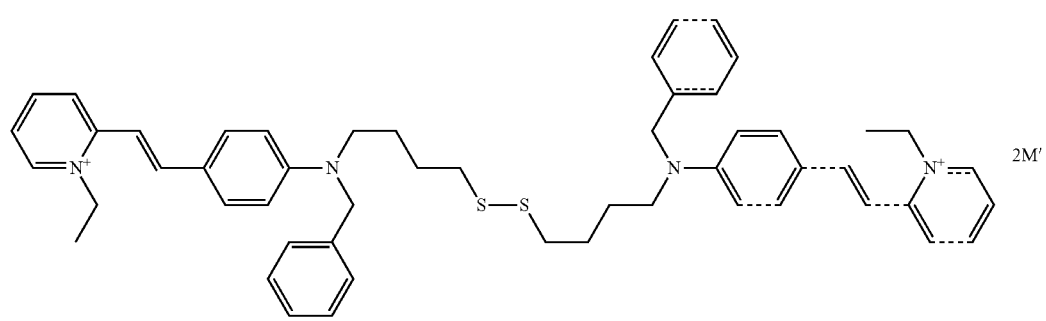

-continued
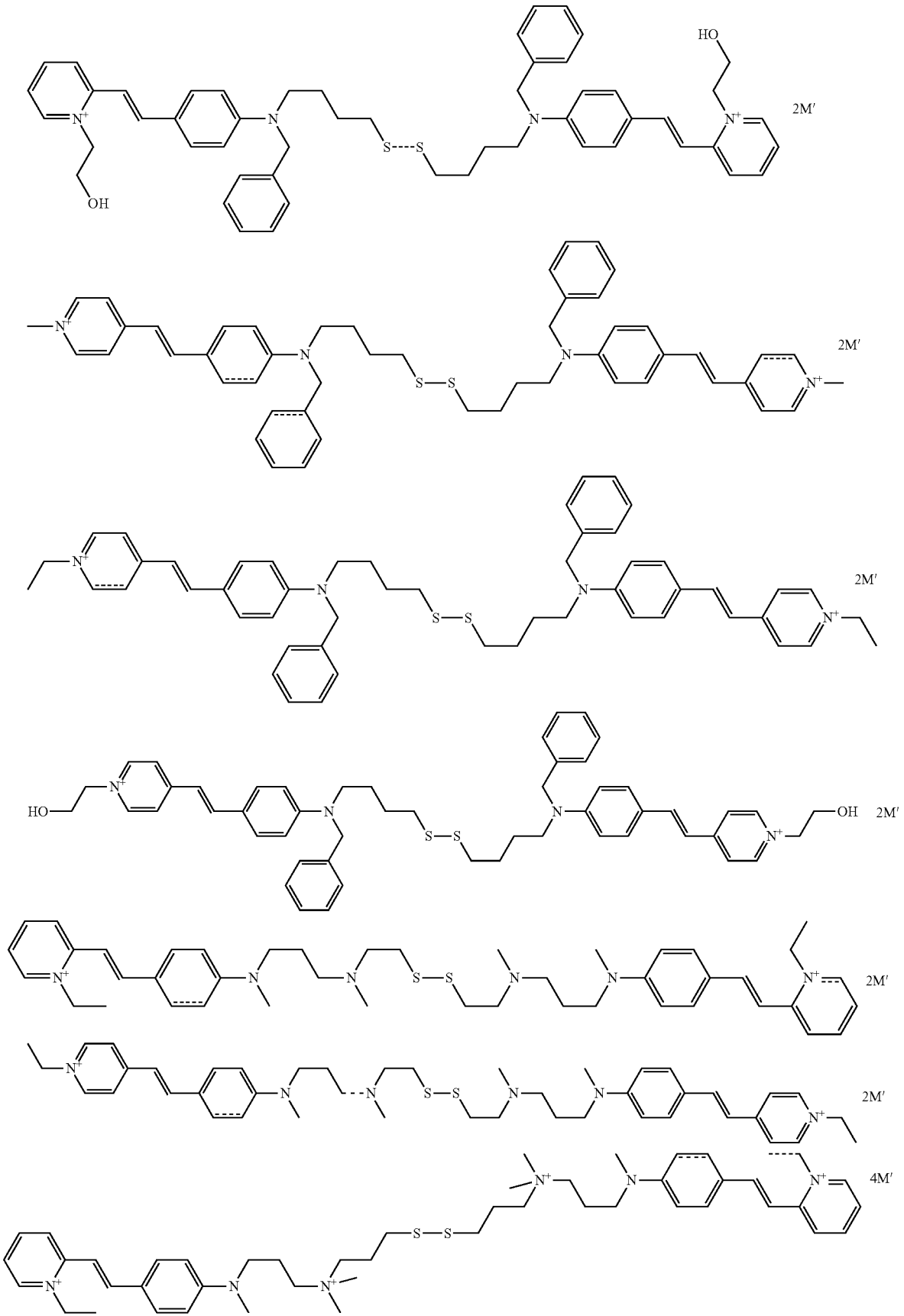

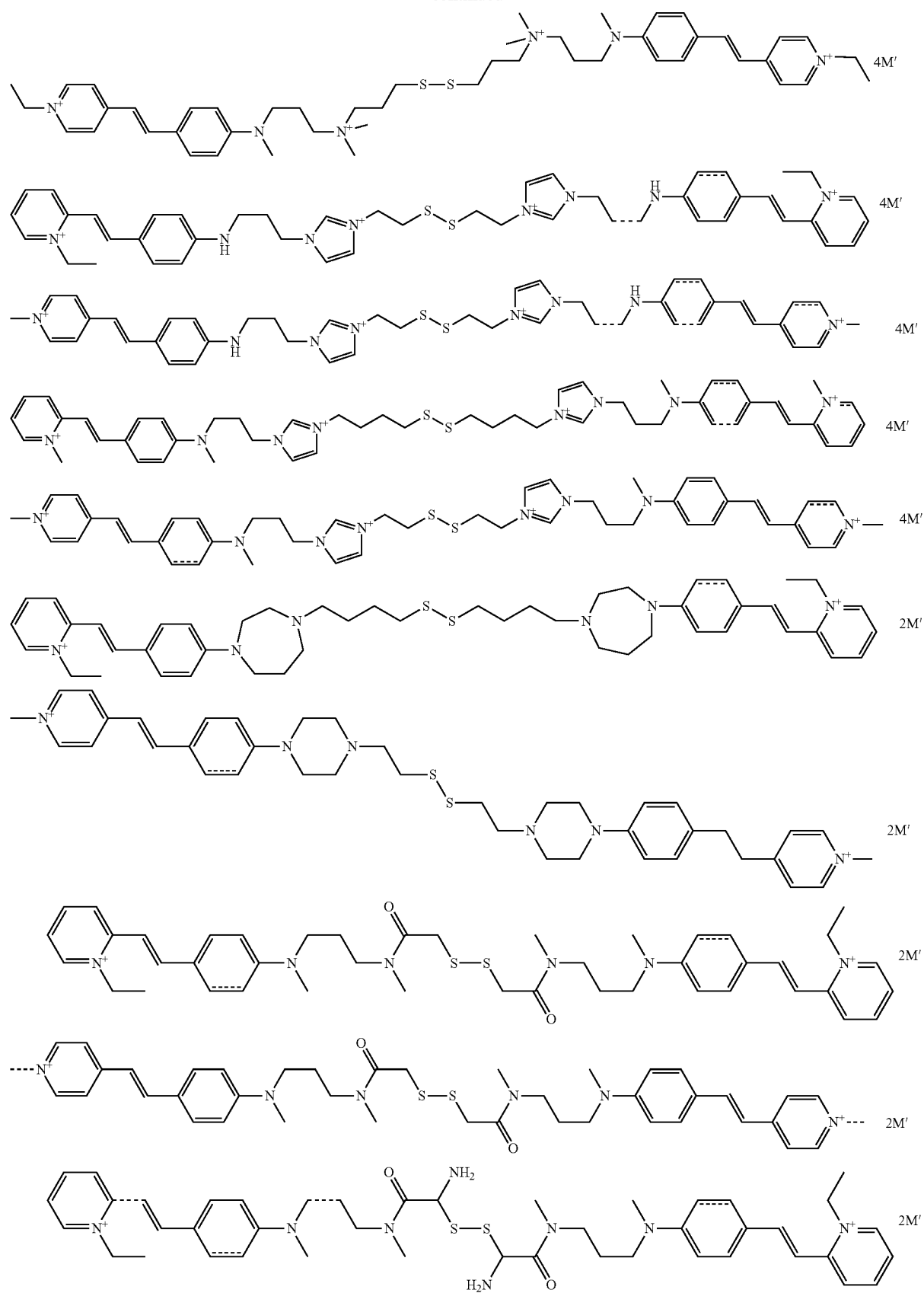

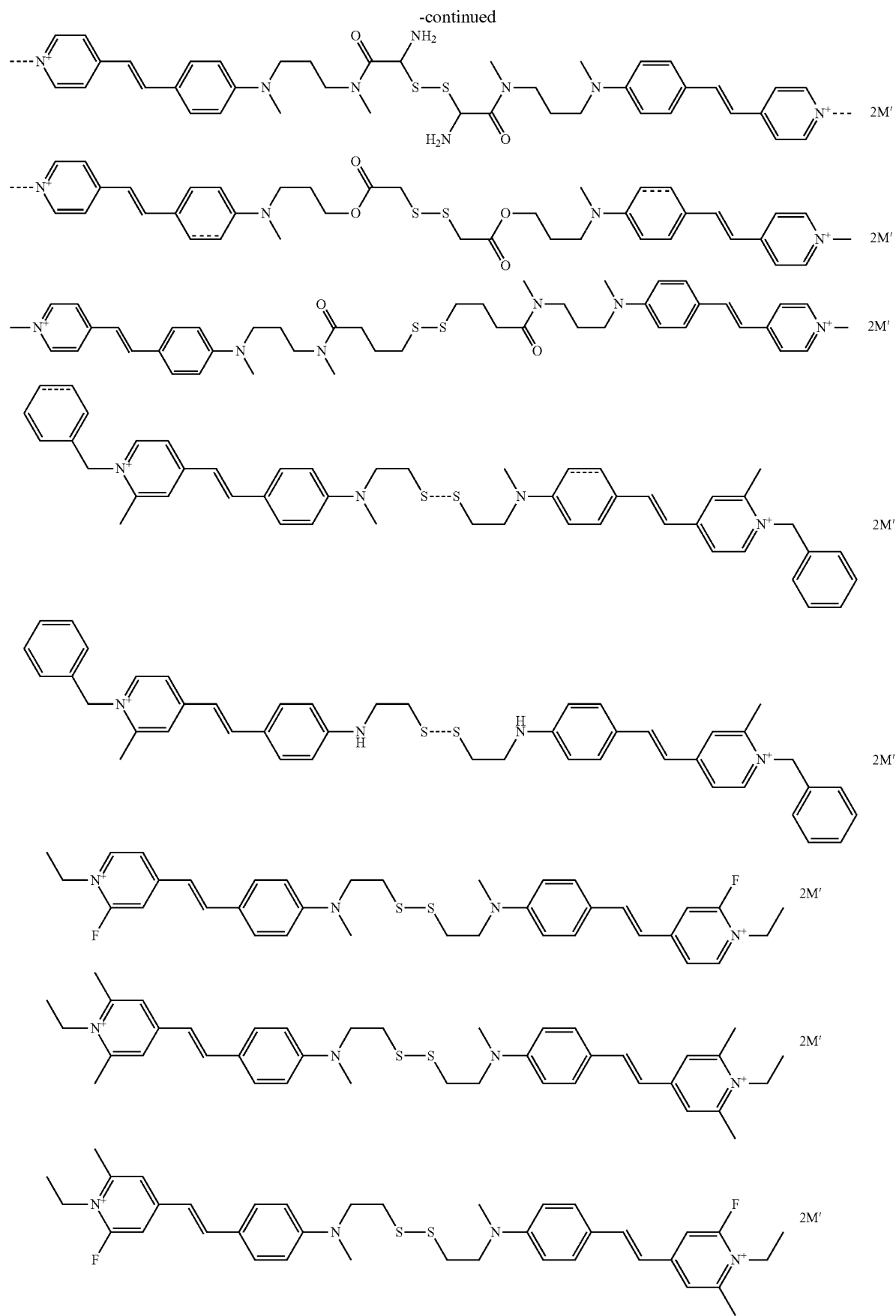
-continued

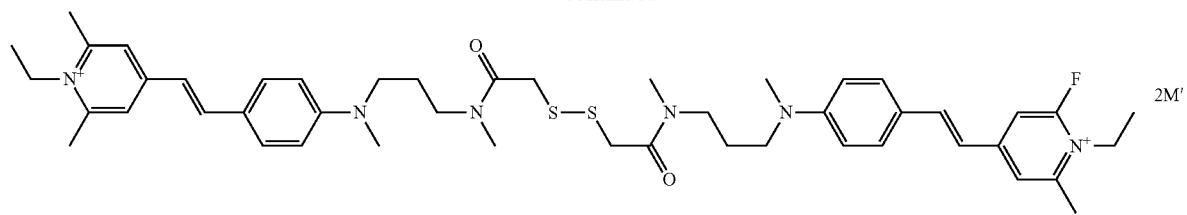
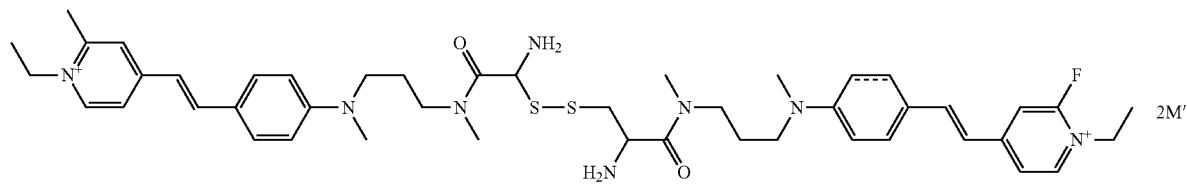
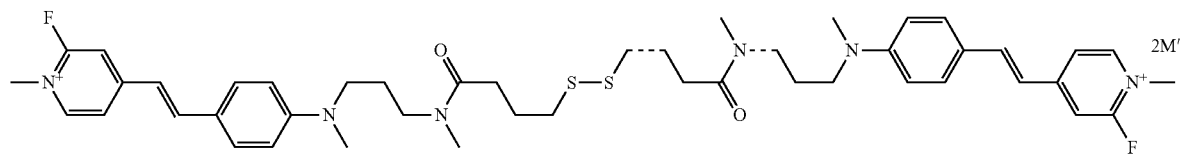
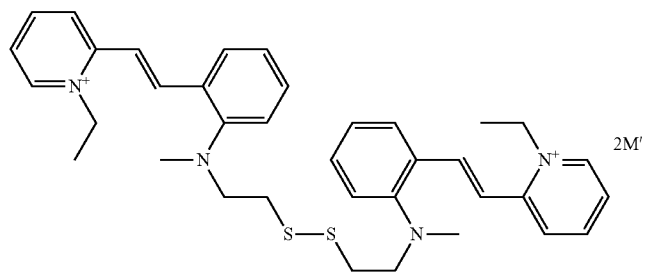
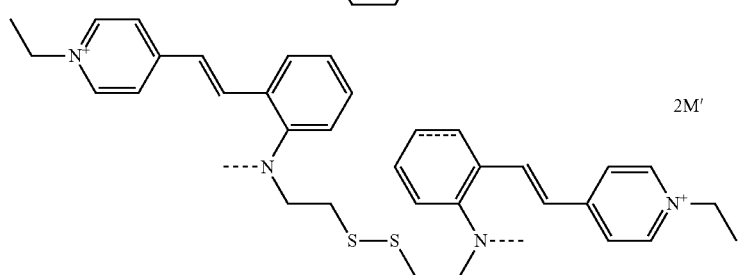
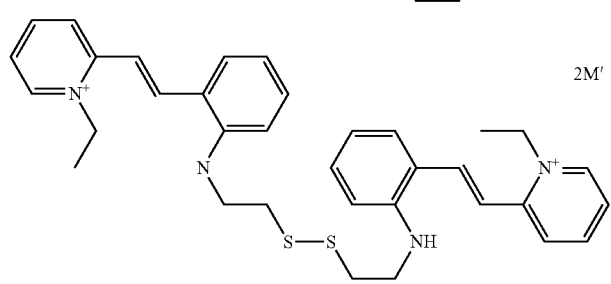
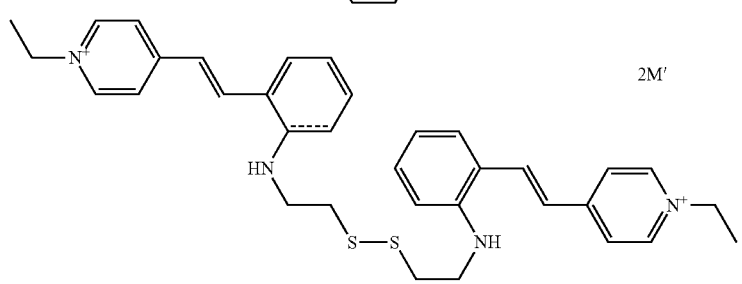

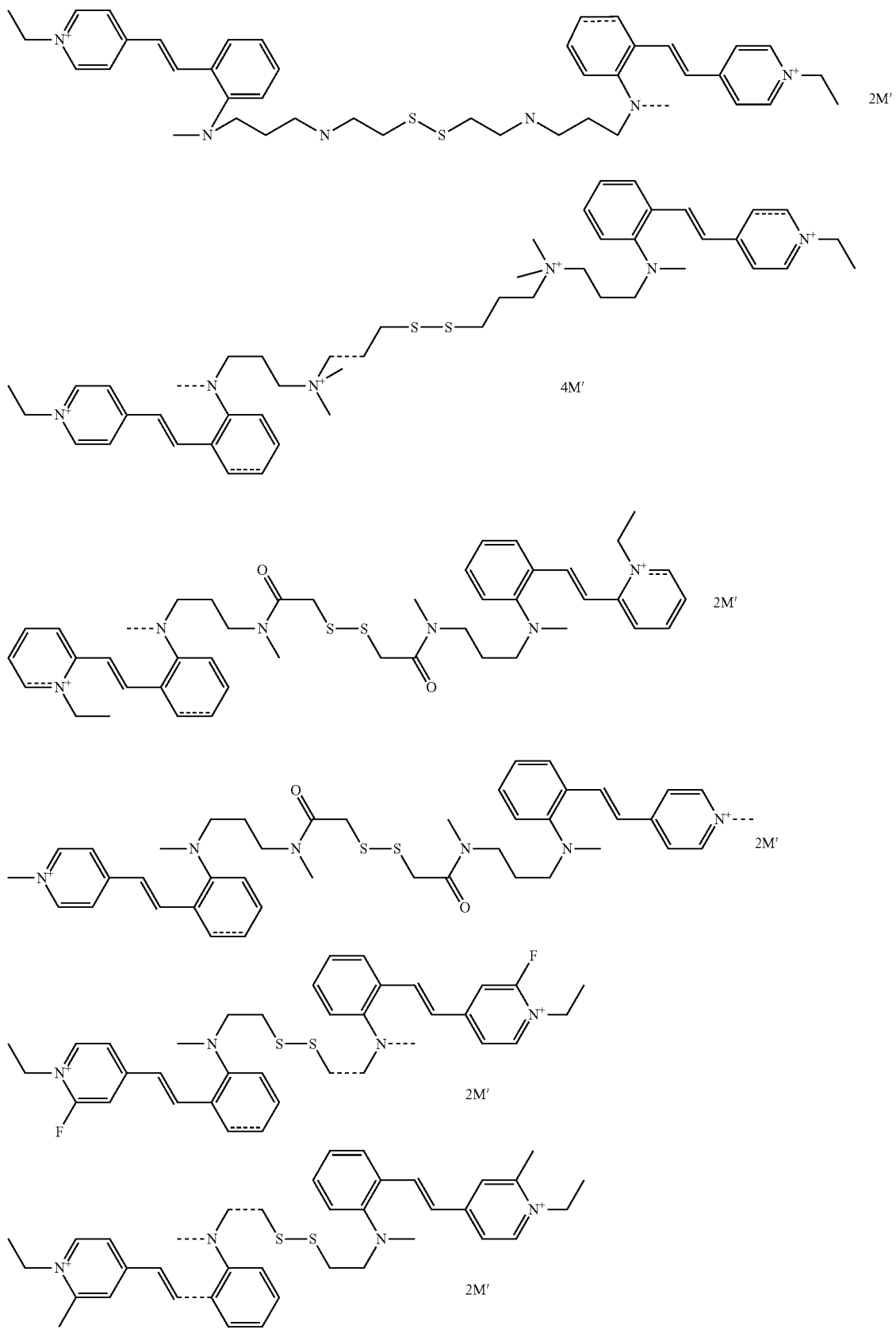

-continued
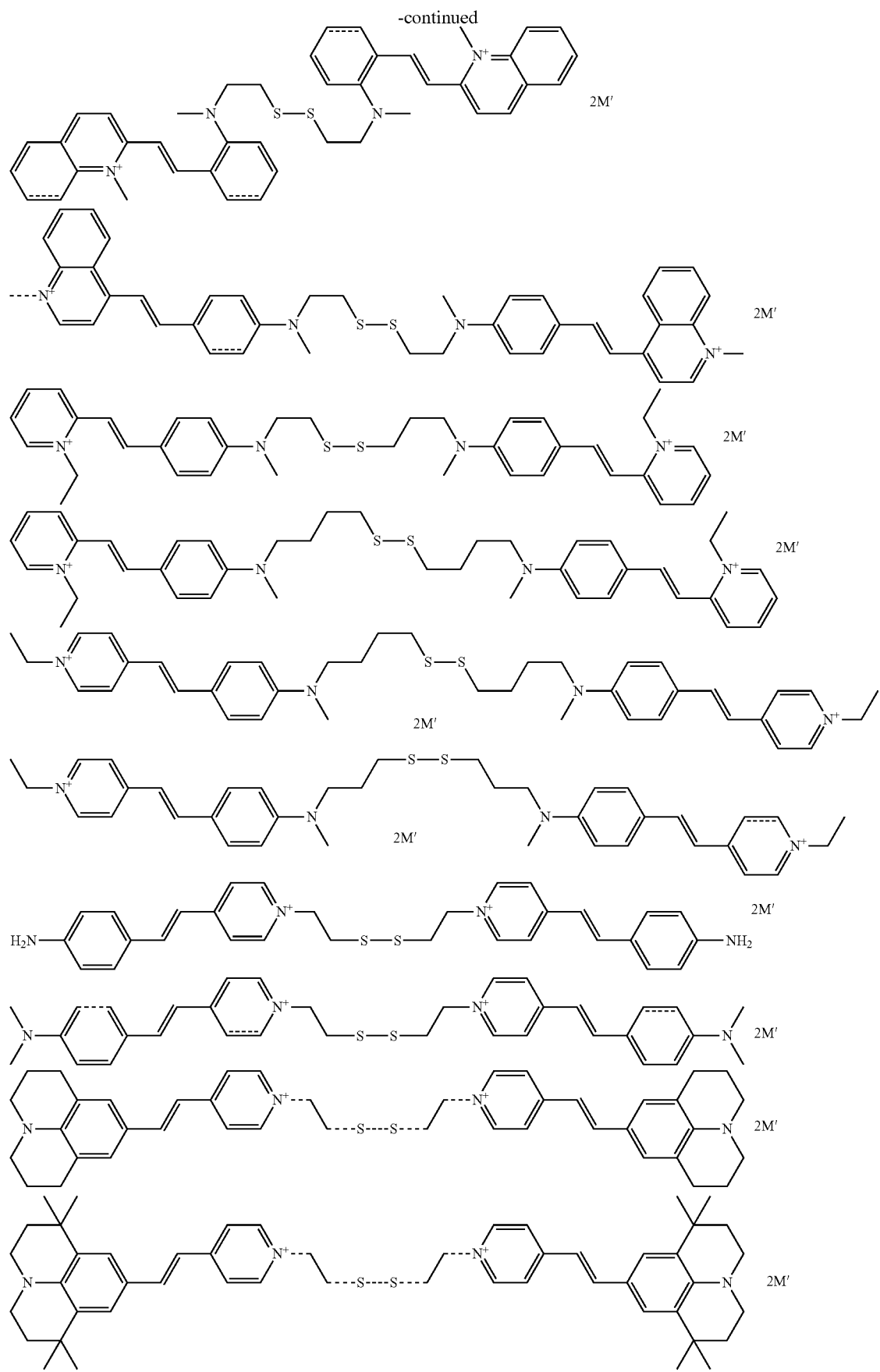

-continued
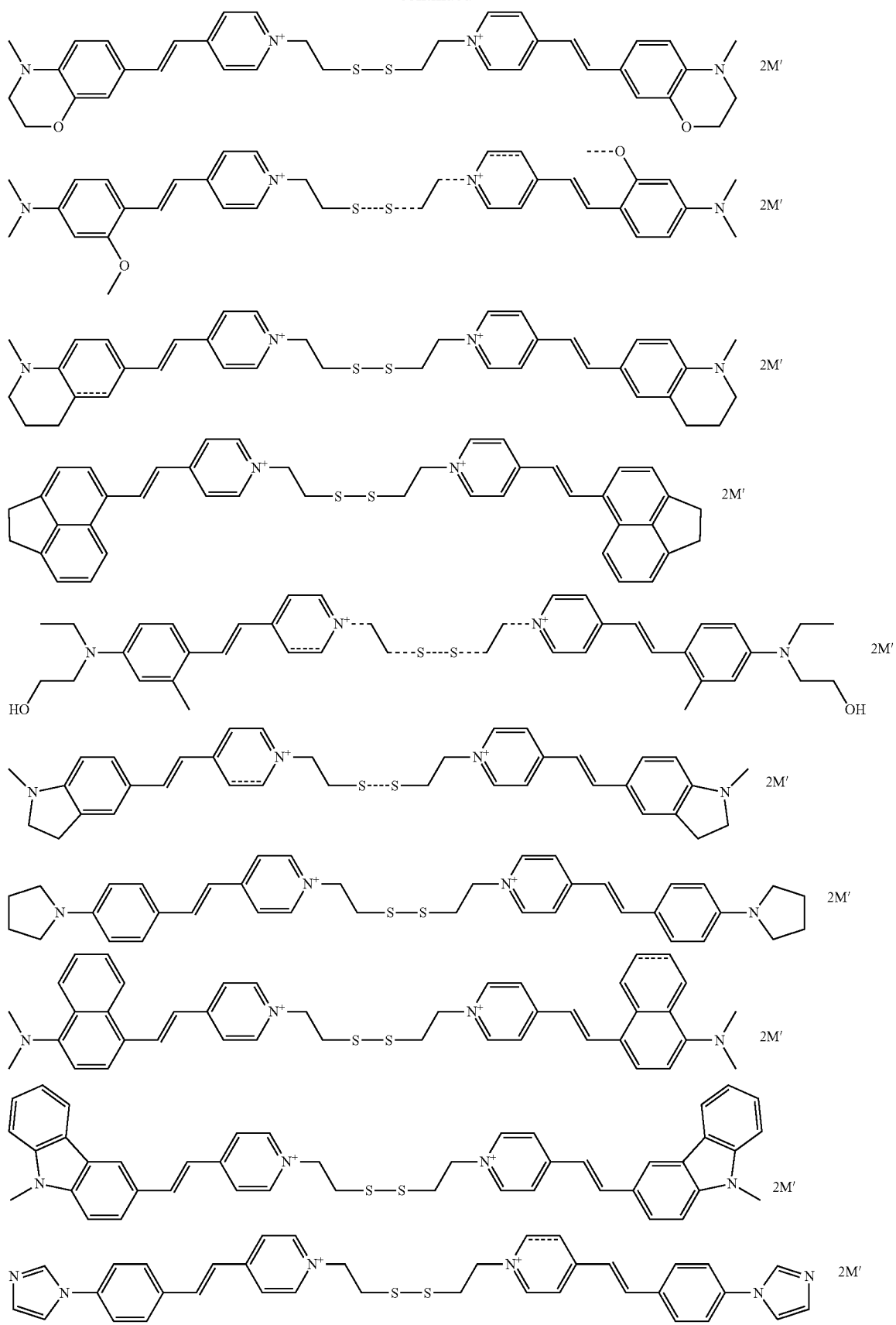

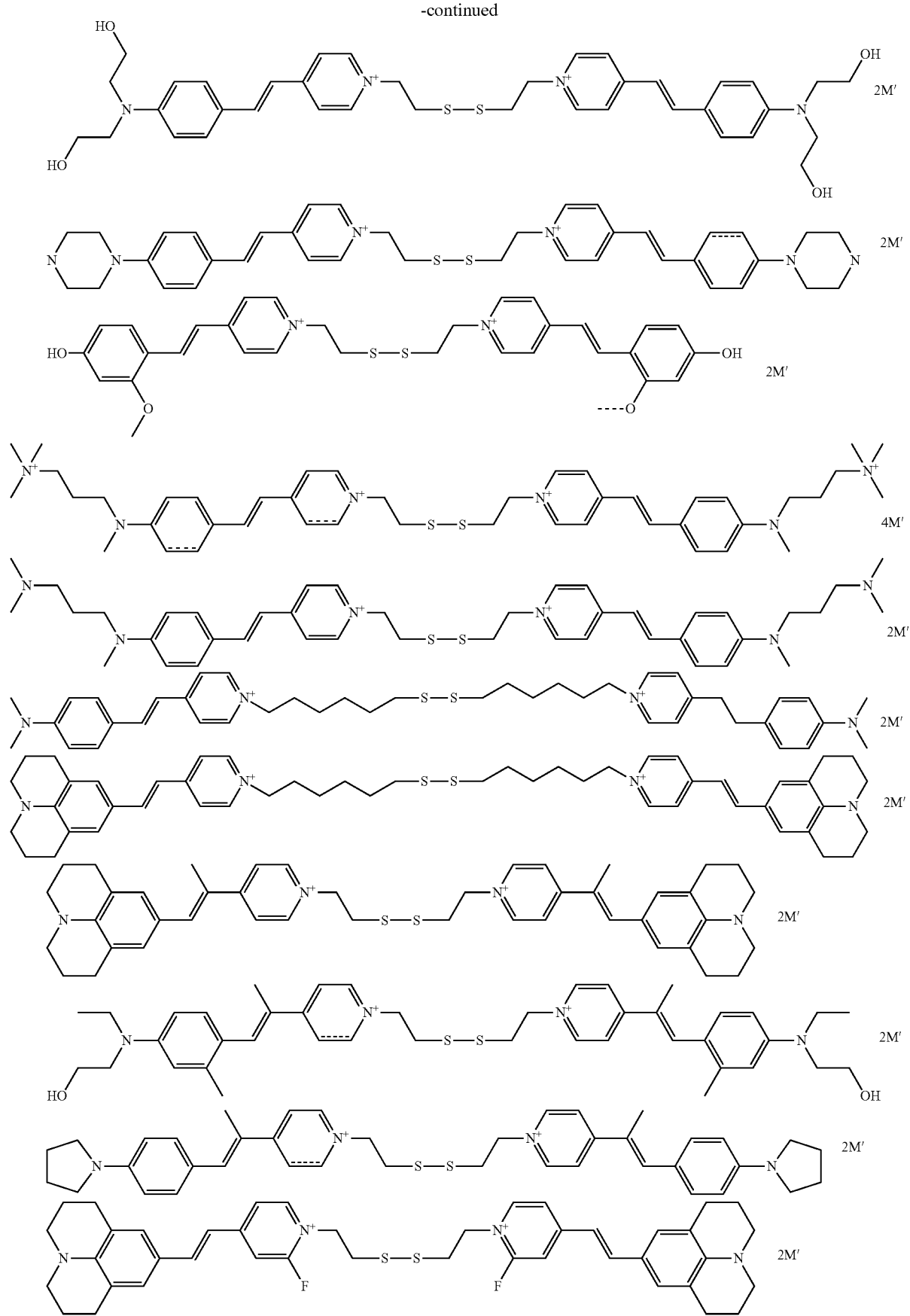

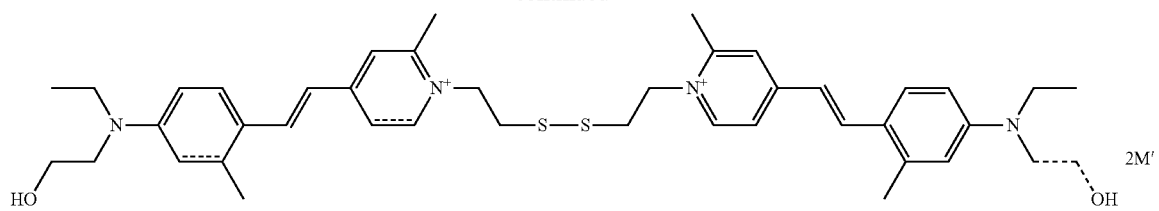
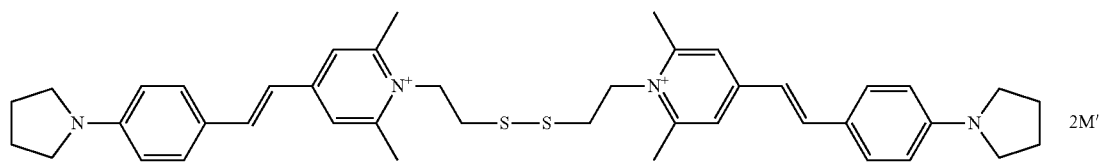
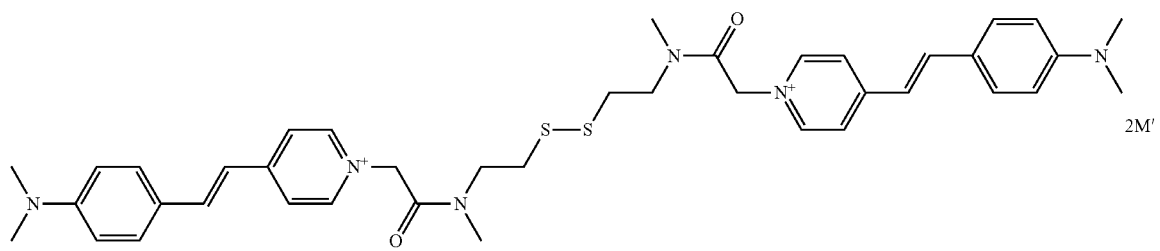
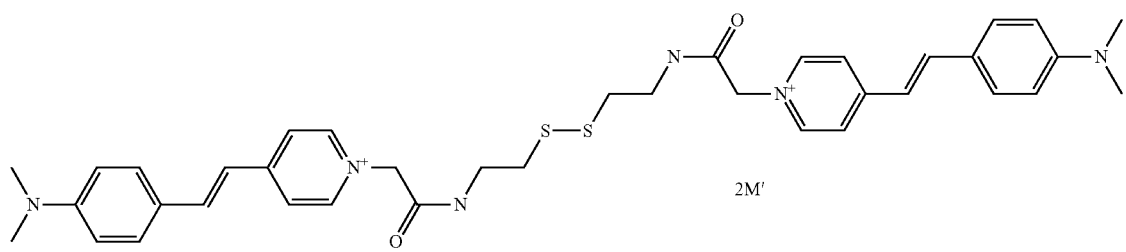
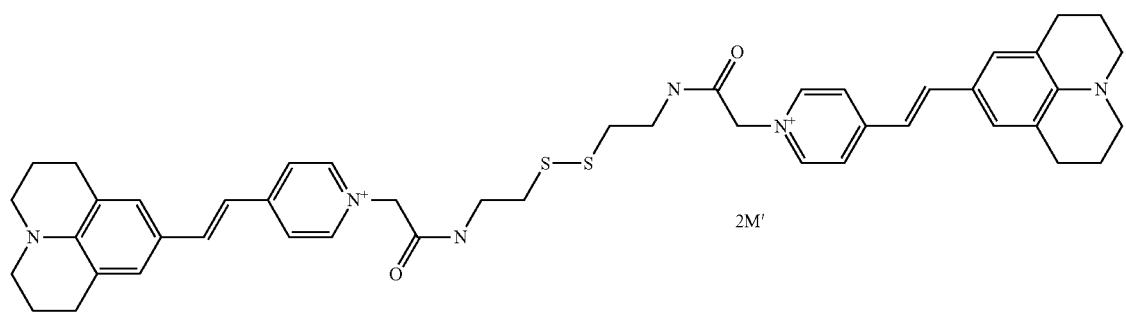
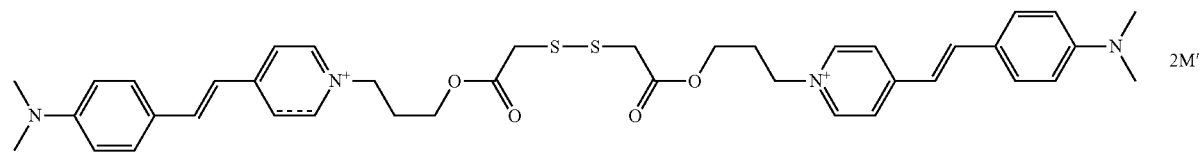
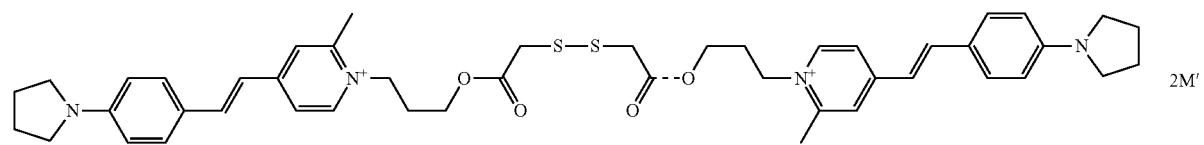
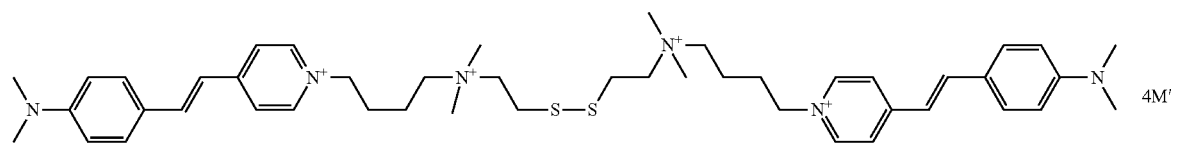

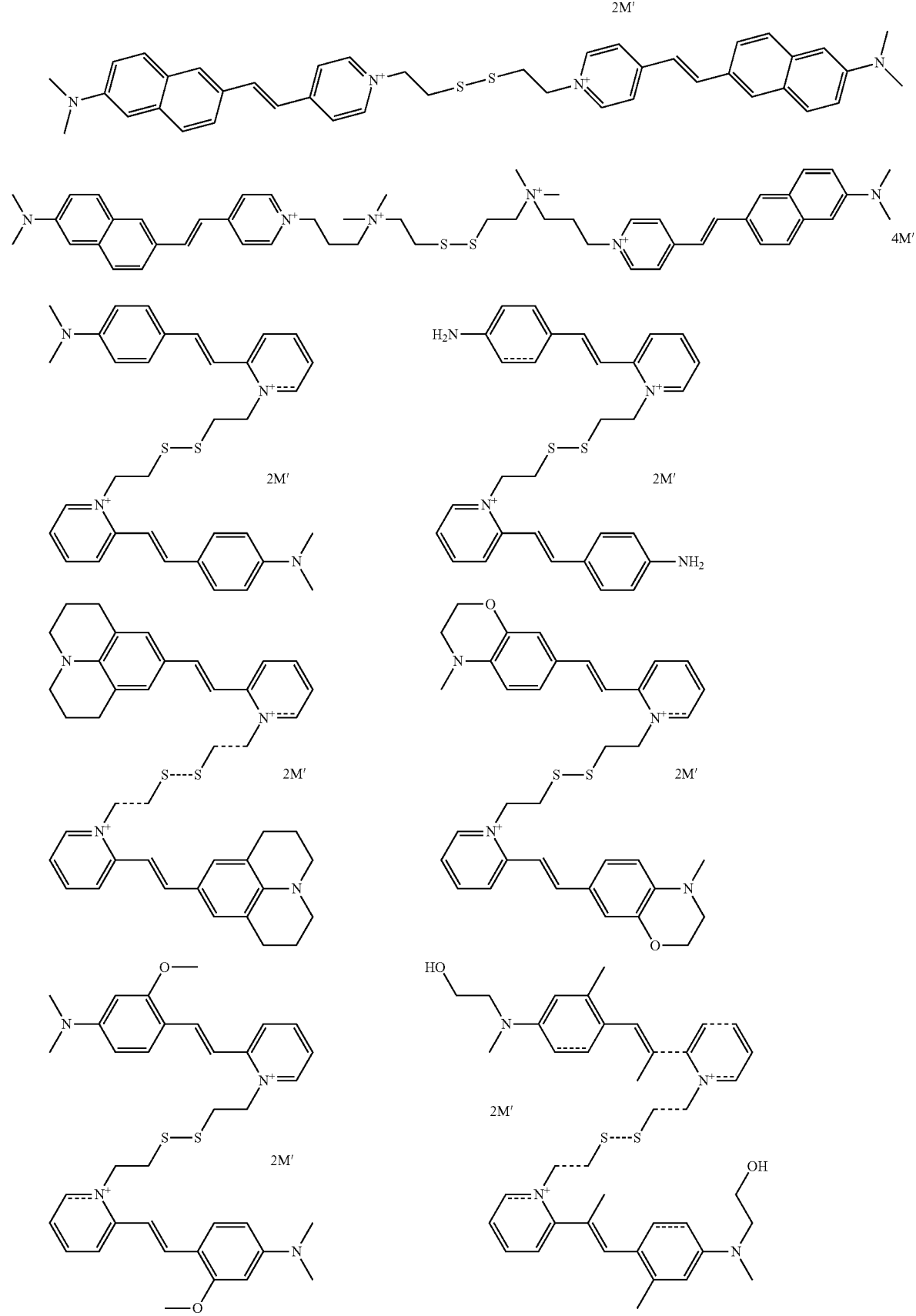

47
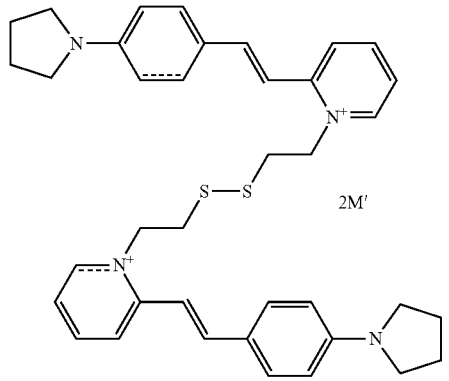
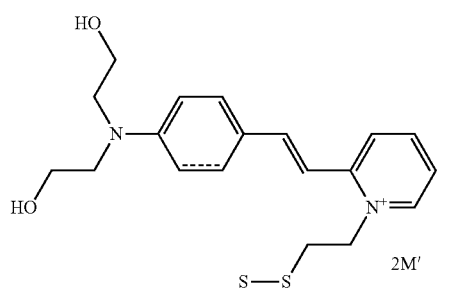
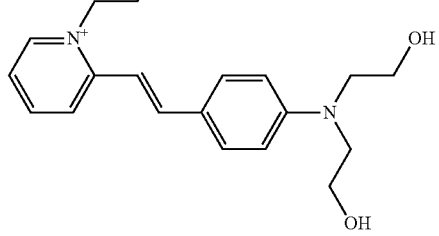
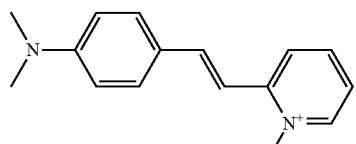
48
-continued
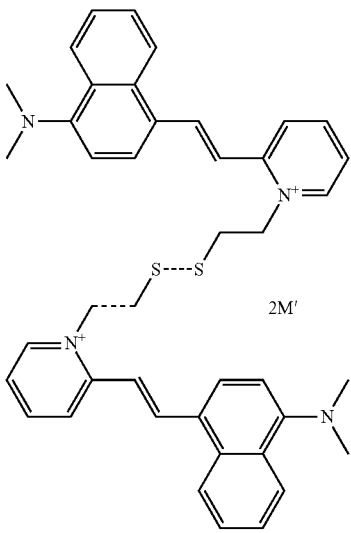
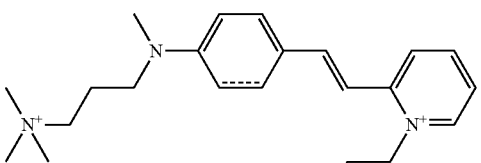
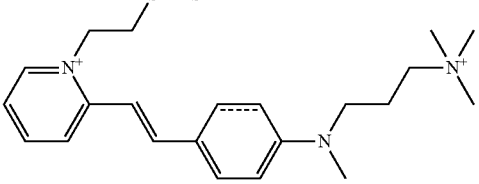
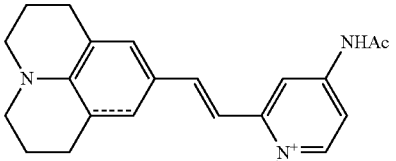
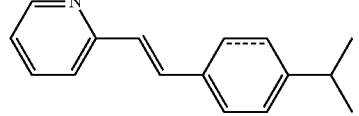

-continued
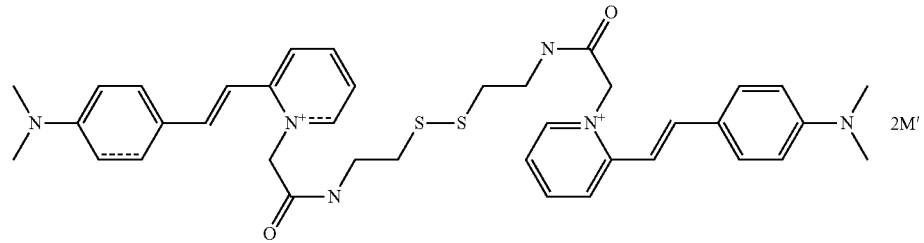
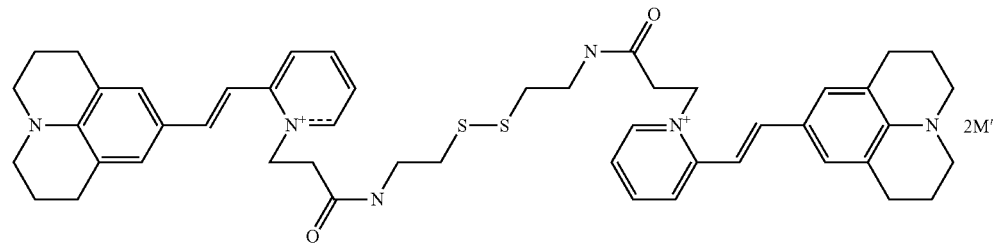
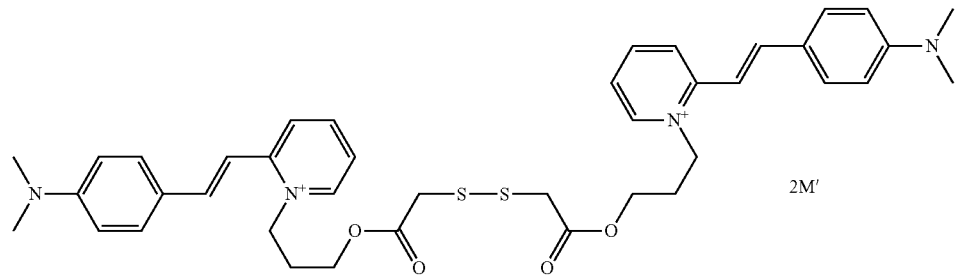
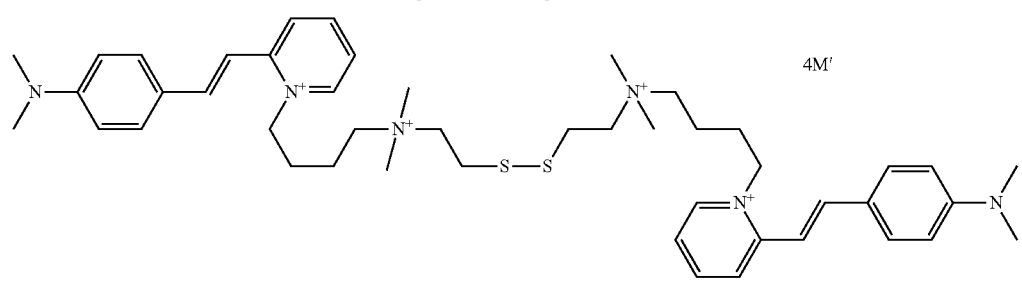
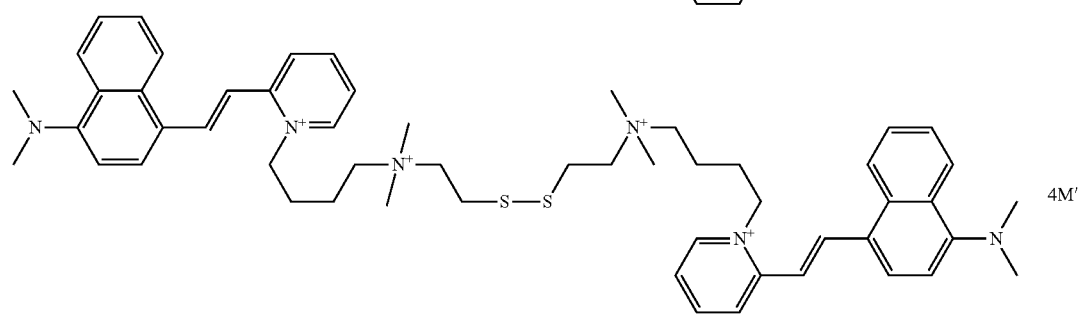
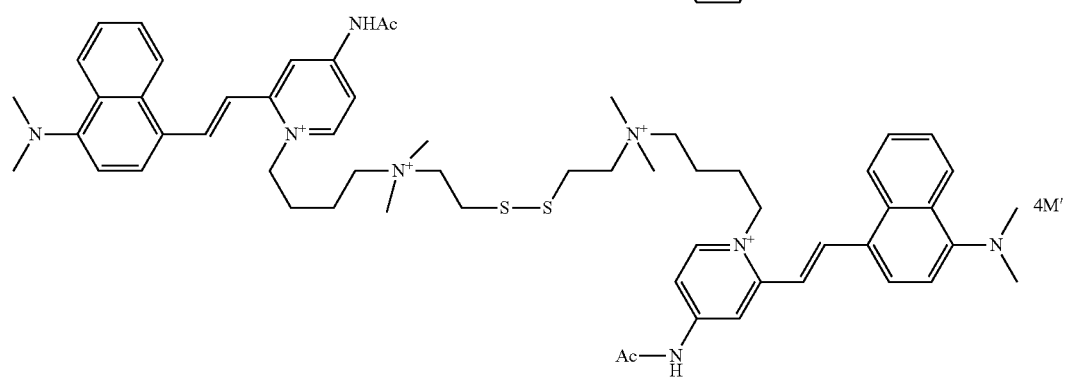

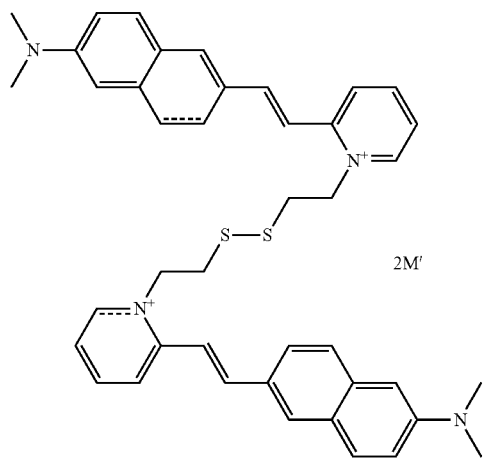
2M'
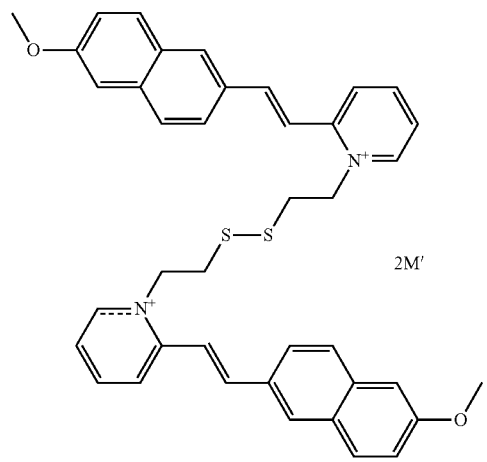
2M'
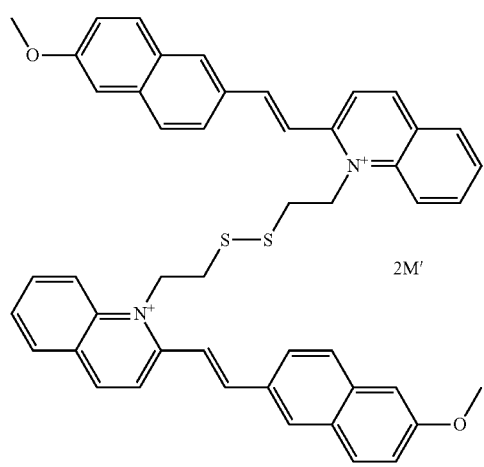
2M'
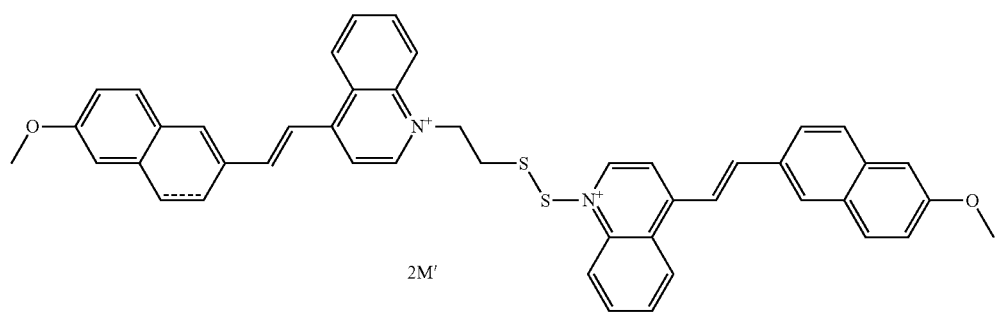
2M'
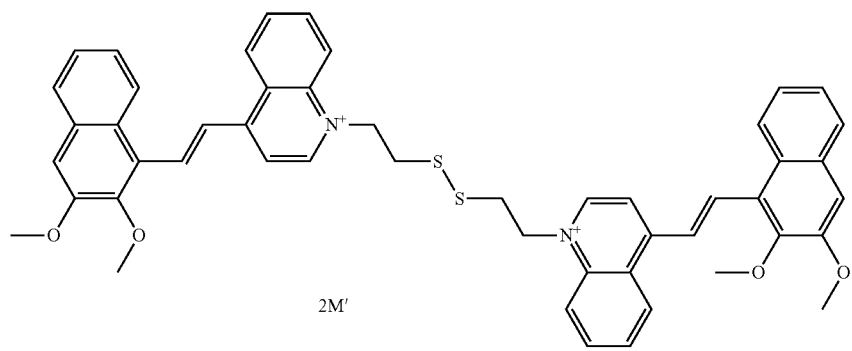
2M'

-continued
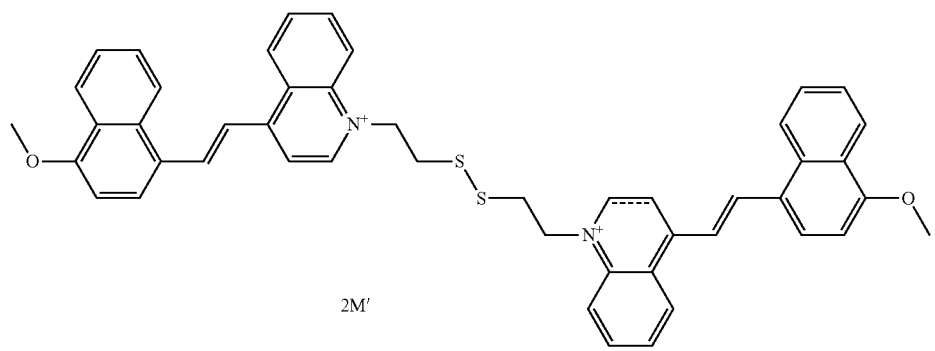
2M′
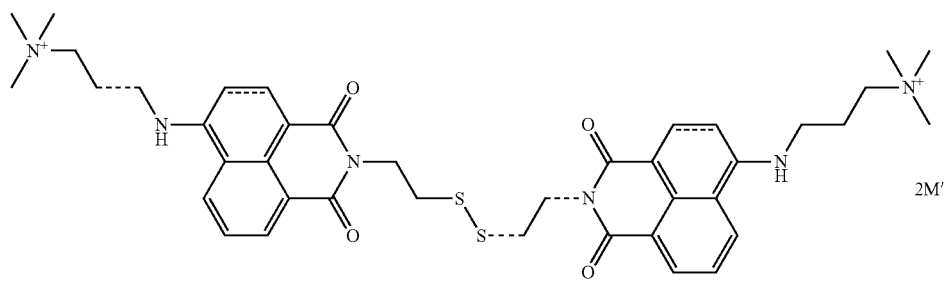
2M′
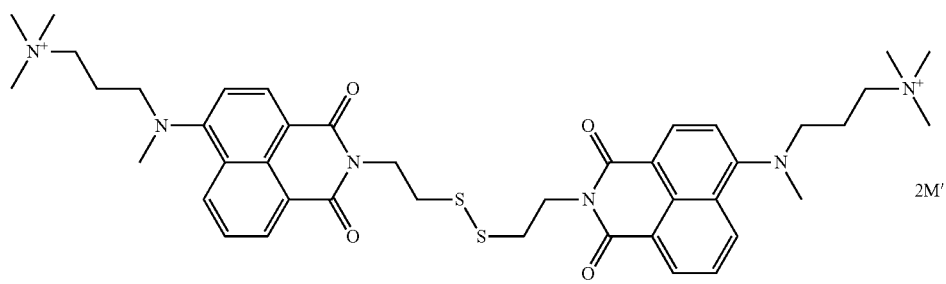
2M′
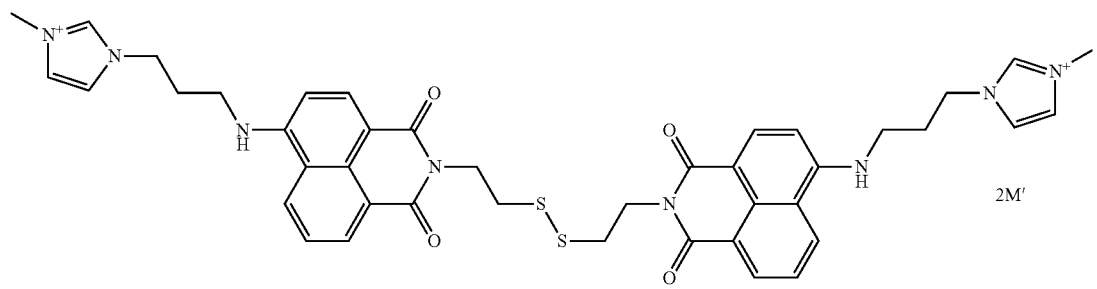
2M′
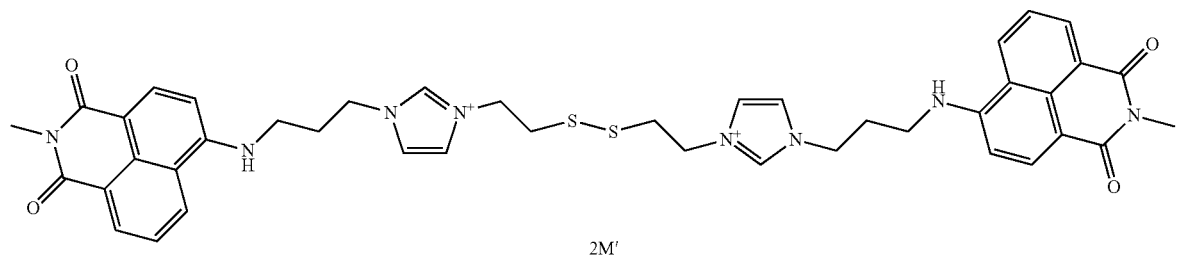
2M′
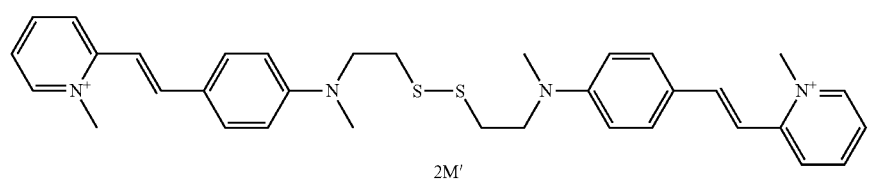
2M′

-continued
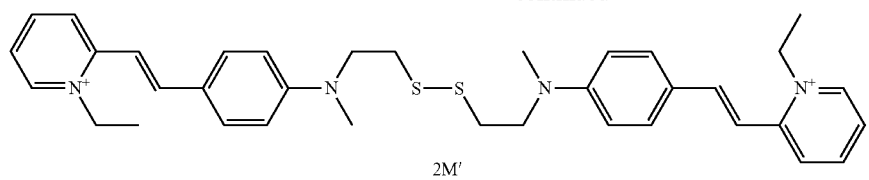
2M'
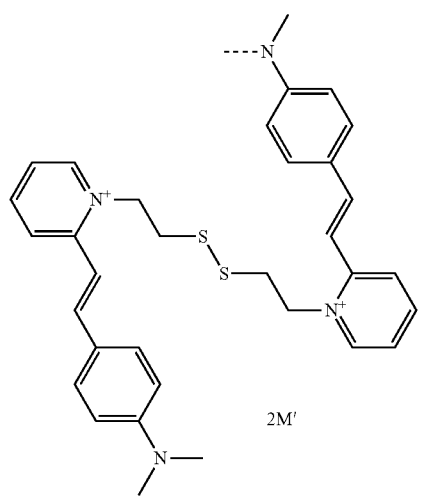
2M'
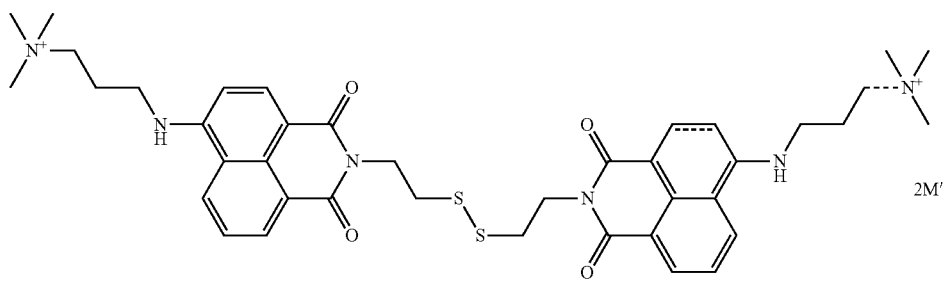
2M'
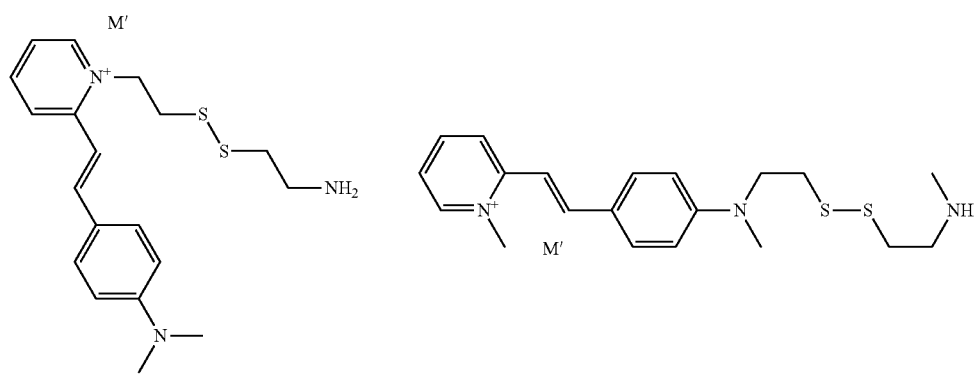
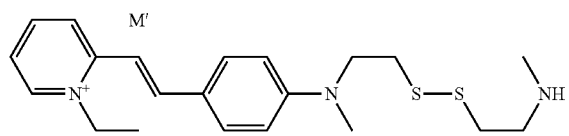
M'
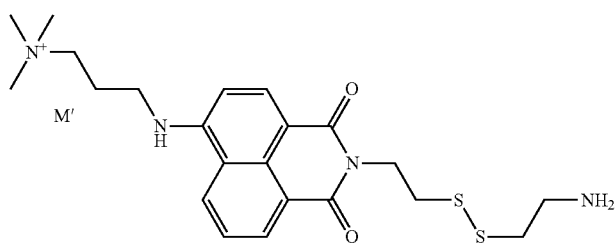
M'

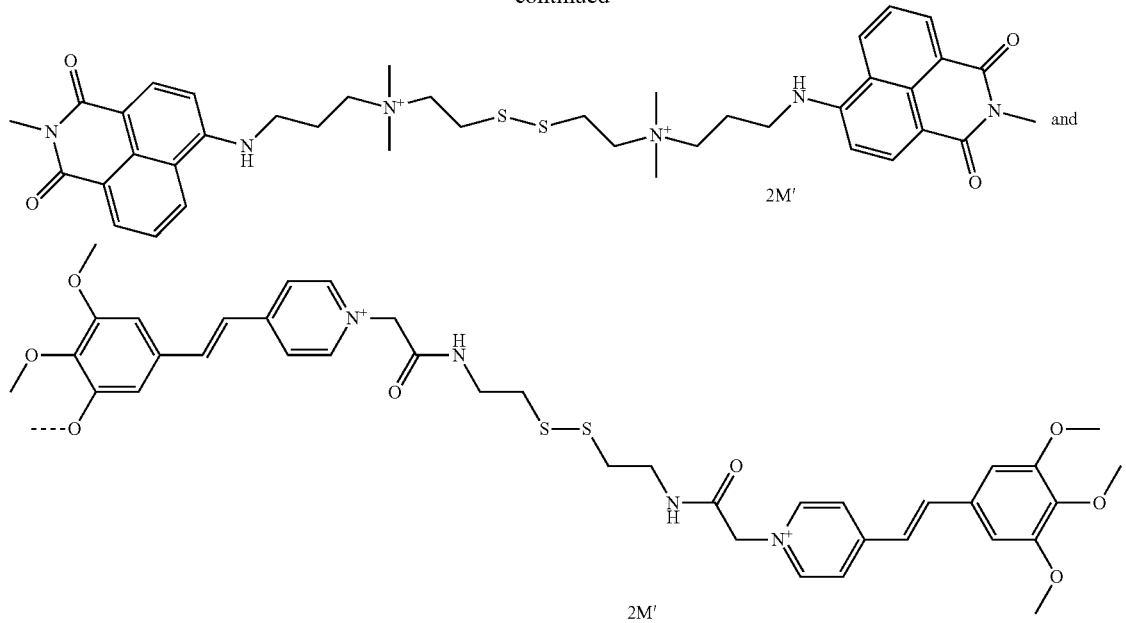

where M' is an anionic counterion.

I.5. The Organic Salt and Counterion:

An "organic or inorganic acid salt" is selected more particularly from a salt derived i) from hydrochloric acid HCl, ii) from hydrobromic acid HBr, iii) from sulphuric acid $H_2SO_4$, iv) from alkylsulphonic acids: Alk-S(O)$_2$OH such as methylsulphonic acid and ethylsulphonic acid; v) from arylsulphonic acids: Ar—S(O)$_2$OH such as benzenesulphonic acid and toluenesulphonic acid; vi) from citric acid; vii) from succinic acid; viii) from tartaric acid; ix) from lactic acid, x) from alkoxysulphinic acids: Alk-O—S(O)OH such as methoxysulphinic acid and ethoxysulphinic acid; xi) from aryloxysulphinic acids such as tolueneoxysulphinic acid and phenoxysulphinic acid; xii) from phosphoric acid $H_3PO_4$; xiii) from acetic acid $CH_3COOH$; xiv) from triflic acid $CF_3SO_3H$ and xv) from tetrafluoroboric acid $HBF_4$.

An "anionic counterion" is an anion or an anionic group which is combined with the cationic charge of the dye; more particularly the anionic counterion is selected from i) halides such as chloride and bromide; ii) nitrates; iii) sulphonates, including $C_1$-$C_6$ alkylsulphonates: Alk-S(O)$_2$O$^-$ such as methylsulphonate or mesylate and ethylsulphonate; iv) arylsulphonates: Ar—S(O)$_2$O$^-$ such as benzenesulphonate and toluenesulphonate or tosylate; v) citrate; vi) succinate; vii) tartrate; viii) lactate; ix) alkyl sulphites: Alk-O—S(O)O$^-$ such as methylsulphite and ethyl sulphite; x) aryl sulphites: Ar—O—S(O)O$^-$ such as benzene sulphite and toluene sulphite; xi) alkyl sulphates: Alk-O—S(O)$_2$O$^-$ such as methyl sulphate and ethyl sulphate; xii) aryl sulphates: Ar—O—S(O)$_2$O$^-$, xiii) phosphate; xiv) acetate; xv) triflate; and xvi) borates such as tetrafluoroborate.

I.6. Preparation of Fluorescent Disulphide Dyes:

The fluorescent disulphide dyes may be prepared by methods which are known to a person skilled in the art.

According to a first possibility a disulphide compound containing two amine functions, preferably primary or secondary amine functions, can be reacted with a sufficient amount of a "reactive fluorescent chromophore" or of a compound containing such a "reactive fluorescent chromophore", in other words containing an electrophilic function.

"Reactive fluorescent chromophores" include reactive dyes containing more particularly a vinyl sulphone, sulphatoethyl sulphone, mono- or dichlorotriazine, mono- or dichloropyrimidine, difluorochloropyrimidine, dichloroquinoxaline or bromovinyl sulphone function.

Also suitable as reactive chromophores are fluorescent chromophore compounds containing at least one group which is capable of reacting with an amine function to give a sulphamide (—SO$_2$—NR—) or amide (—CO—NR—) group. For example, mention may be made of the groups —SO$_3$W' and —COOW' (where W' represents a hydrogen atom, an alkali metal, such as sodium or potassium, an ammonium group, an ammonium group which is substituted by one or more identical or non-identical, linear or branched, $C_1$-$C_{10}$ alkyl groups which optionally carry at least one hydroxyl), which may be activated beforehand, by known methods, to form respectively an —SO$_2$Cl or —COCl group.

Consideration may also be given to employing, as the reactive fluorescent chromophore, the Colour Index acid dyes that are listed as being such.

Reference may be made more particularly to Advanced Organic Chemistry, March, 4th Edition, for further details on the operating conditions employed.

Still within the context of this first possibility, it is possible to employ fluorescent chromophores comprising a labile group which is bonded directly or not to the fluorescent chromophore and can be substituted by an amine group, such as Cl, Br, F, O-alkyl (for example O-Me), O-aryl, O-alkylaryl (for example O-benzyl).

In the context of this possibility, the fluorescent disulphide dyes may also be obtained by using chromophores possessing an acrylate function (—OOO—C═C—), on which an addition reaction is carried out.

In accordance with another possibility, the fluorescent disulphide dyes may be obtained by reacting a disulphide compound with a compound which carries two carboxylic acid functions which are activated by conventional methods (for example, reaction with a carbodiimide or with thionyl chloride). The resulting product is then reacted with a fluorescent chromophore which carries a nucleophilic function, of primary or secondary amine type for example, or of aliphatic or aromatic alcohol type such as phenol.

Here again, reference may be made to Advanced Organic Chemistry, March, 4th Edition, for further details on the operating conditions employed.

In accordance with a third possibility, the fluorescent disulphide dyes may be obtained by reacting a compound containing a disulphide group and two hydroxyl groups which are activated beforehand to form leaving groups (for example mesylate or tosylate) with a fluorescent chromophore which carries a nucleophilic function, advantageously of primary, secondary or tertiary, heteroaromatic or non-heteroaromatic type, for example of pyridine, imidazole or benzimidazole type.

In accordance with a fourth possibility, the fluorescent disulphide dyes may be obtained by controlled oxidation of dyes which carry an SH function.

In accordance with a fifth possibility, and particularly for the preparation of compounds corresponding to the formula (II), the fluorescent disulphide dyes may be obtained by a variant of possibilities one, two or three described above, by using a molar quantity of disulphide reagent that is greater than or equal to the molar quantity of reagent containing the chromophore group.

The preparation of fluorescent disulphide dyes corresponding to the formula (I) for which A and A' are identical is made easier, on the other hand, by the use of a molar quantity of reagent containing the fluorescent chromophore group that is preferably greater than or equal to two times the amount of disulphide reagents.

In accordance with a sixth possibility, and particularly for the preparation of compounds corresponding to the formula (I) in which the two groups A and A' on the one hand and X and X' on the other hand are different, the disulphide compounds may be obtained from fluorescent disulphide compounds corresponding to the formula (II).

II. Dyeing Composition:

II.1. Dyes:

The dyeing composition used in the invention generally contains an amount of fluorescent disulphide dye of between 0.001% and 50% relative to the total weight of the composition. Preferably this amount is between 0.005% and 20% by weight and more preferably still between 0.01% and 5% by weight relative to the total weight of the composition.

The dyeing composition may further comprise additional direct dyes. These direct dyes are selected for example from neutral, acidic or cationic nitrobenzene direct dyes, neutral, acidic or cationic azo direct dyes, tetraazapentamethine dyes, quinone dyes and more particularly neutral, acidic or cationic anthraquinone dyes, azine direct dyes, triarylmethane direct dyes, indoamine direct dyes and natural direct dyes.

The natural direct dyes include lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes, and more particularly henna-base poultices or extracts.

The dyeing composition may contain one or more oxidation bases and/or one or more couplers that are conventionally used for the dyeing of keratin fibres.

The oxidation bases include para-phenylenediamines, bisphenylalkylene-diamines, para-aminophenols, bis-para-aminophenols, ortho-aminophenols, hetero-cyclic bases and their addition salts.

These couplers may include, more particularly, meta-phenylenediamines, meta-aminophenols, meta-diphenols, naphthalene couplers, heterocyclic couplers and their additional salts.

The coupler or couplers are each generally present in an amount of between 0.001% and 10% by weight of the total weight of the dyeing composition, preferably between 0.005% and 6%.

The oxidation base or bases which are present in the dyeing composition are generally each present in an amount of between 0.001% to 10% by weight of the total weight of the dyeing composition, preferably between 0.005% and 6% by weight.

Generally speaking, the addition salts of the oxidation bases and of the couplers than can be used in the context of the invention are selected more particularly from the addition salts with an acid, such as hydrochlorides, hydrobromides, sulphates, citrates, succinates, tartrates, lactates, tosylates, benzenesulphonates, phosphates and acetates, and the addition salts with a base, such as alkali metal hydroxides, for instance sodium hydroxide and potassium hydroxide, aqueous ammonia, amines or alkanolamines.

The medium appropriate for dyeing, also referred to as a dyeing vehicle, is a cosmetic medium which is generally composed of water or of a mixture of water and at least one organic solvent. Organic solvents include, for example, $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, and also aromatic alcohols such as benzyl alcohol or phenoxyethanol, and mixtures thereof.

The solvents, when present, are present preferably in proportions of preferably between 1% and 40% by weight, approximately, relative to the total weight of the dyeing composition, and more preferably still between 5% and 30% by weight, approximately.

In one variant the invention contains a reducing agent which is capable of reducing the disulphide bonds. This reducing agent is as defined above.

II.2. Adjuvants:

The dyeing composition may also include various adjuvants which are conventionally used in hair dyeing compositions, such as anionic, cationic, nonionic, amphoteric and zwitterionic surfactants or mixtures thereof, anionic, cationic, nonionic, amphoteric and zwitterionic polymers or mixtures thereof, organic or inorganic thickeners, and especially anionic, cationic, nonionic and amphoteric polymeric associative thickeners, antioxidants, penetrants, sequestrants, fragrances, buffers, dispersants, conditioning agents such as, for example, volatile or non-volatile, modified or non-modified silicones, such as amino silicones, film formers, ceramides, preservatives, opacifiers and conductive polymers.

Amount of Adjuvants:

The adjuvants above are generally present in an amount, for each of them, of between 0.01% and 20% by weight relative to the weight of the composition.

A person skilled in the art would of course take care to select this or these complementary compounds in such a way that the advantageous properties intrinsically attaching to the dyeing composition in accordance with the invention are not, or not substantially, adversely affected by the intended addition or additions.

pH

The pH of the dyeing composition is generally between 3 and 14 approximately, and preferably between 5 and 11 approximately. It may be adjusted to the desired value by means of acidifying or alkalifying agents which are commonly used in the dyeing of keratin fibres or else by means of conventional buffer systems.

Acidifying agents include, for example, organic or inorganic acids such as hydrochloric acid, orthophosphoric acid, sulphuric acid, carboxylic acids such as acetic acid, tartaric acid, citric acid and lactic acid, and sulphonic acids. Alkalifying agents include, for example, aqueous ammonia, alkali metal carbonates, alkanolamines such as mono-, di- and tri-ethanolamines and their derivatives, sodium hydroxide or potassium hydroxide, and the compounds of formula

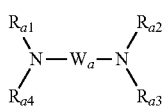
(α)

in which $W_a$ is a propylene residue which is optionally substituted by a hydroxyl group or a $C_1$-$C_4$ alkyl radical, and $R_{a1}$, $R_{a2}$, $R_{a3}$ and $R_{a4}$, which are identical or different, each represent a hydrogen atom or a $C_1$-$C_4$ alkyl or $C_1$-$C_4$ hydroxyalkyl radical.

II.3. Forms of the Composition:

The dyeing composition may be presented in various forms, such as in the form of a liquid, cream or gel, or in any other form which is appropriate for performing the dyeing of keratin fibres, and more particularly of the hair.

III. Colouring Method:

The dyeing composition is generally applied at ambient temperature. It may, however, be carried out at temperatures ranging from 20 to 180° C.

In one particular colouring method of the invention, the fluorescent disulphide dye is applied to the keratin materials at the same time as a reducing agent. The reducing agent is as defined above.

In another variant, the reducing agent is added to the dyeing composition containing the fluorescent disulphide dyes (I) and (II) at the time of use.

In accordance with another variant, the method of the invention may be implemented in the presence of a post-treatment oxidizing agent when the composition already contains a reducing agent.

The oxidizing agent may be any oxidizing agent which is conventionally used in the art. Hence it may be selected from hydrogen peroxide, urea peroxide, alkali metal bromates, persalts such as perborates and persulphates, and also enzymes, among which mention may be made of peroxidases, 2-electron oxidoreductases such as uricases, and 4-electron oxygenases such as laccases. The use of hydrogen peroxide is particularly preferred.

This oxidizing agent may be applied to the fibres before or after the application of the composition containing the fluorescent disulphide dyes of formulae (I) and (II).

IV. Dyeing Device or Kit.

The invention further provides a multi-compartment dyeing device or kit, in which a first compartment contains a dyeing composition comprising at least one fluorescent disulphide dye of formulae (I) or (II) and a second compartment contains a reducing agent capable of reducing the disulphide bond of the dye and/or the disulphide functions of the keratin materials.

One of these compartments may further contain one or more other dyes of direct dye or oxidation dye type.

The invention further pertains to a multi-compartment device in which a first compartment contains a dyeing composition comprising at least one fluorescent disulphide dye of formulae (I) or (II), a second compartment contains a reducing agent capable of reducing the disulphide bond of the dye, and a third compartment contains an oxidizing agent.

Each of the aforementioned devices may be equipped with means allowing the desired mixture to be delivered to the hair, such as, for example, the devices described in patent FR2 586 913.

The examples which follow serve to illustrate the invention, but without exhibiting any limitative nature. The fluorescent disulphide dyes in the examples below were entirely characterized by conventional spectrometric and spectroscopic methods.

EXAMPLES

Synthesis Examples

Example 1

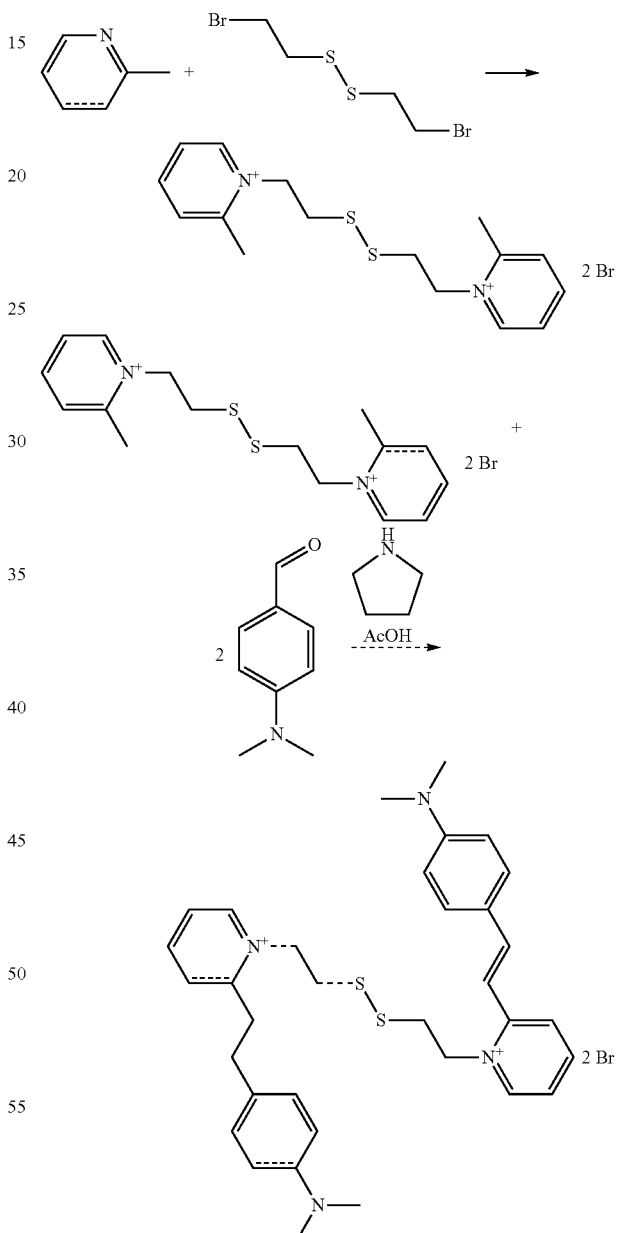

Step 1: 1,1'-(Disulphanediyldiethane-2,1-diyl)bis(2-methylpyridinium)dibromide

A mixture of 56 g of 1-bromo-2-[(2-bromoethyl)disulphanyl]ethane and 15 ml of N-methylpyrrolidone (NMP) is introduced dropwise into 35 g of 2-picoline with stirring at 80° C. The mixture (white suspension) is kept with stirring at 80° C. for 30 minutes, 100 ml of acetonitrile are added, and stirring is maintained at 80° C. for 90 minutes. After cooling, the solid obtained is filtered off, washed with 100 ml of acetonitrile and then dried.

This gives 56.2 g of brown powder. 45 g of this powder are suspended in 300 ml of isopropanol at reflux. When the temperature has dropped to 40° C., the solid is filtered off, washed with 3 times 100 ml of isopropanol and dried under vacuum. Light beige product, 40.56 g. Analyses in accordance with the anticipated structure.

Step 2: 1,1'-(Disulphanediyldiethane-2,1-diyl)bis(2-{(E)-2-[4-(dimethylamino)-phenyl]vinyl}pyridinium)dibromide 150 mg of pyrrolidine and then 129 mg of acetic acid are added to a solution of 297 mg of 4-dimethylaminobenzaldehyde in 2 ml of methanol.

After 18 h of stirring at ambient temperature, 495 mg of 1,1'-(disulphanediyldiethane-2,1-diyl)bis(2-methylpyridinium)dibromide are added to the mixture, and stirring is maintained at ambient temperature for 7 days. Following filtration, washing with methanol and drying under vacuum, 312 mg of orange powder are recovered. Analyses in accordance with the anticipated structure. $^1$H NMR (400 MHz, MeOH-d$_4$): 3.02 (s, 6H), 3.22 (t, 2H), 5 (t, 2H), 6.72 (m, 2H), 7.19 (d, 1H), 7.63 (m, 3H), 7.76 (d, 1H), 8.3 (m, 2H), 8.59 (m, 1H).

Example 2 thylaniline) is added dropwise. The mixture is stirred at 0° C. for 90 minutes and then at 10° C. for 75 minutes and at 40° C. for 105 minutes. It is then poured into 2.5 l of ice-water, and 700 ml of 5N sodium hydroxide are added. The yellow precipitate obtained is filtered off on celite and dissolved in 200 ml of dichloromethane and the resulting solution is washed with 200 ml of saturated aqueous sodium chloride solution. After drying over magnesium sulphate and evaporation of the dichloromethane, the yellow residue (80 g) is purified by chromatography on silica gel.

After drying, a light yellow powder is recovered. The analyses indicate that the product is in accordance with the expected structure.

Step 2: 2,2'-{Disulphanediylbis[ethane-2,1-diyl(methylimino)-4,1-phenylene(E)-ethene-2,1-diyl]}bis(1-methylpyridinium)dichloride 25 g of 4,4'-{disulphanediylbis[ethane-2,1-diyl(methylimino)]}dibenzaldehyde and 18.5 g of N-methylpicolinium chloride are dissolved in 300 ml of methanol. 12.7 ml of piperidine are added to the mixture. The combined system is heated with stirring at 55° C. for 11 hours. The methanol is removed under vacuum at 40° C. The solid is mixed with 300 ml of isopropanol. Following renewed drying by evaporation, 200 ml of isopropanol are introduced. The mixture solidifies, and is extended by adding 100 ml of isopropanol and filtered off with suction on a glass frit. The solid recovered is washed with isopropanol and then with acetone and then dried under vacuum. After drying, 36.7 g of orange powder are recovered.

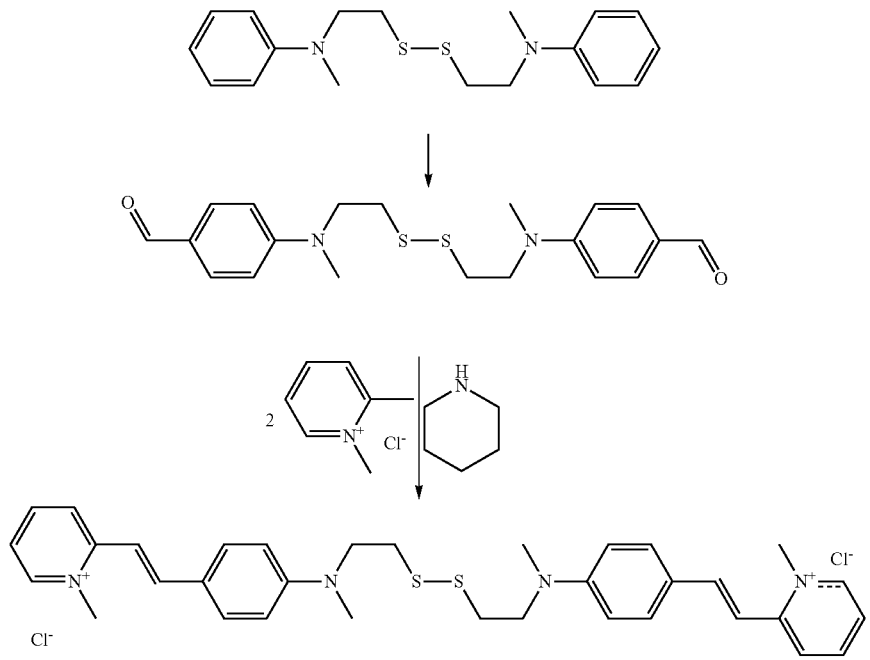

Step 1: 4,4'-{Disulphanediylbis[ethane-2,1-diyl(methylimino)]}dibenzaldehyde 82.3 g of phosphorus oxychloride are added to 500 ml of DMF at 0° C. After 30 minutes of stirring at 0° C., a solution of 47 g of N,N'-(disulphanediyldiethane-2,1-diyl)bis(N-me- By recrystallization from isopropanol, 27 g of high-purity orange-red powder are recovered. The analyses indicate that the product is in accordance with specification and is pure. $^1$H NMR (400 MHz, MeOH-d$_4$) 2.99 (t, 4H), 3.81 (t, 4H), 4.31 (s, 6H), 6.86 (d, 4H), 7.22 (d, 2H), 7.63 (m, 2H), 7.69 (d, 4H), 7.83 (d, 2H), 8.29 (m, 2H), 8.36 (m, 2H), 8.61 (m, 2H).

Example 3

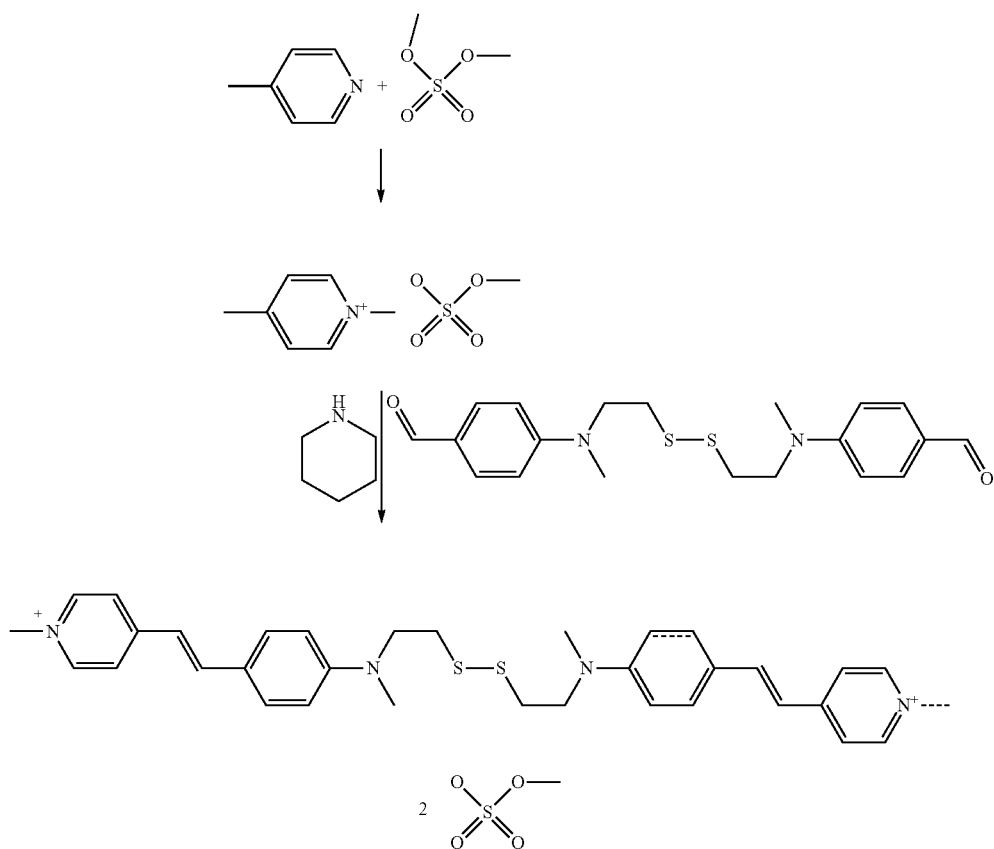

4,4'-{Disulphanediylbis[ethane-2,1-diyl(methylimino)-4,1-phenylene(E)ethene-2,1-diyl]}bis(1-methylpyridinium)dimethoxysulphate 2.62 g of 4-picoline are diluted in 25 ml of dichloromethane, and 3 ml of dimethyl sulphate are added to this solution, whose temperature rises to reflux (40° C.). After 40 minutes of stirring, 50 ml of isopropanol are added, and the mixture is concentrated by distillation of the dichloromethane (mixture heated at 60° C.). 1.83 g of pyrrolidine are introduced into the mixture, followed by 4.99 g of 4,4'-{disulphanediylbis[ethane-2,1-diyl(methylimino)]}dibenzaldehyde. After 2 hours of stirring at 65° C., the reaction mixture is cooled to ambient temperature and the precipitate formed is filtered off and washed with 3 times 100 ml of isopropanol. The red paste obtained is dispersed in 200 ml of isopropanol, and the mixture thus obtained is heated to reflux and then cooled. The red precipitate formed is filtered off and then dried. 8.94 g of red powder are recovered. The analyses indicate that the product is in accordance with specification and pure. $^1$H NMR (400 MHz, DMSO-$d_6$) 2.96 (t, 4H), 3.02 (s, 6H), 3.36 (s, 6H), 3.72 (t, 4H), 4.16 (s, 6H), 6.81 (d, 4H), 7.15 (d, 2H), 7.57 (d, 4H), 7.87 (d, 2H), 8.02 (d, 4H), 8.66 (d, 4H).

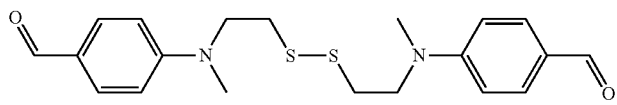

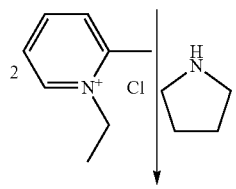

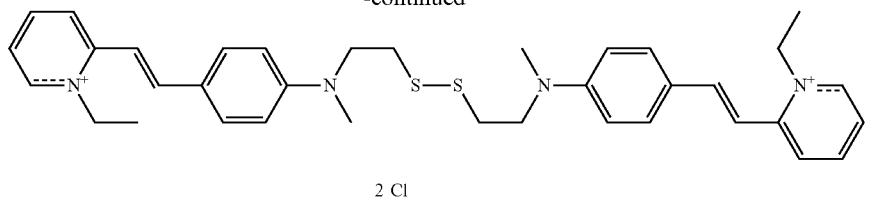

Example 4

2,2'-{Disulphanediylbis[ethane-2,1-diyl(methylimino)-4,1-phenylene(E)ethene-2,1-diyl]}bis(1-ethylpyridinium)dichloride 10 g of 4,4'-{disulphanediylbis[ethane-2,1-diyl(methylimino)]}dibenzaldehyde and 8.1 g of N-ethylpicolinium chloride are dissolved in 100 ml of isopropanol. 1.3 g of piperidine are added to the mixture. The combined system is heated with stirring at reflux for 5 hours. The isopropanol is removed under vacuum at 50° C. The gum obtained is triturated with acetone. 18 g of solid are recovered and are treated with carbon black. 7.1 g of product are collected, and 4 g are purified by liquid/liquid (water/BuOH) chromatography. After drying, 1.65 g of red powder are recovered. The analyses indicate that the product is in accordance with specification and pure. $^1$H NMR (400 MHz, MeOH-$d_4$) 1.57 (t, 6H), 2.98 (t, 4H), 3.11 (s, 6H), 3.8 (t, 4H), 4.73 (q, 4H), 6.85 (m, 4H), 7.23 (d, 2H), 7.69 (m, 6H), 7.85 (d, 2H), 8.29 (m, 2H), 8.38 (m, 2H), 8.67 (m, 2H).

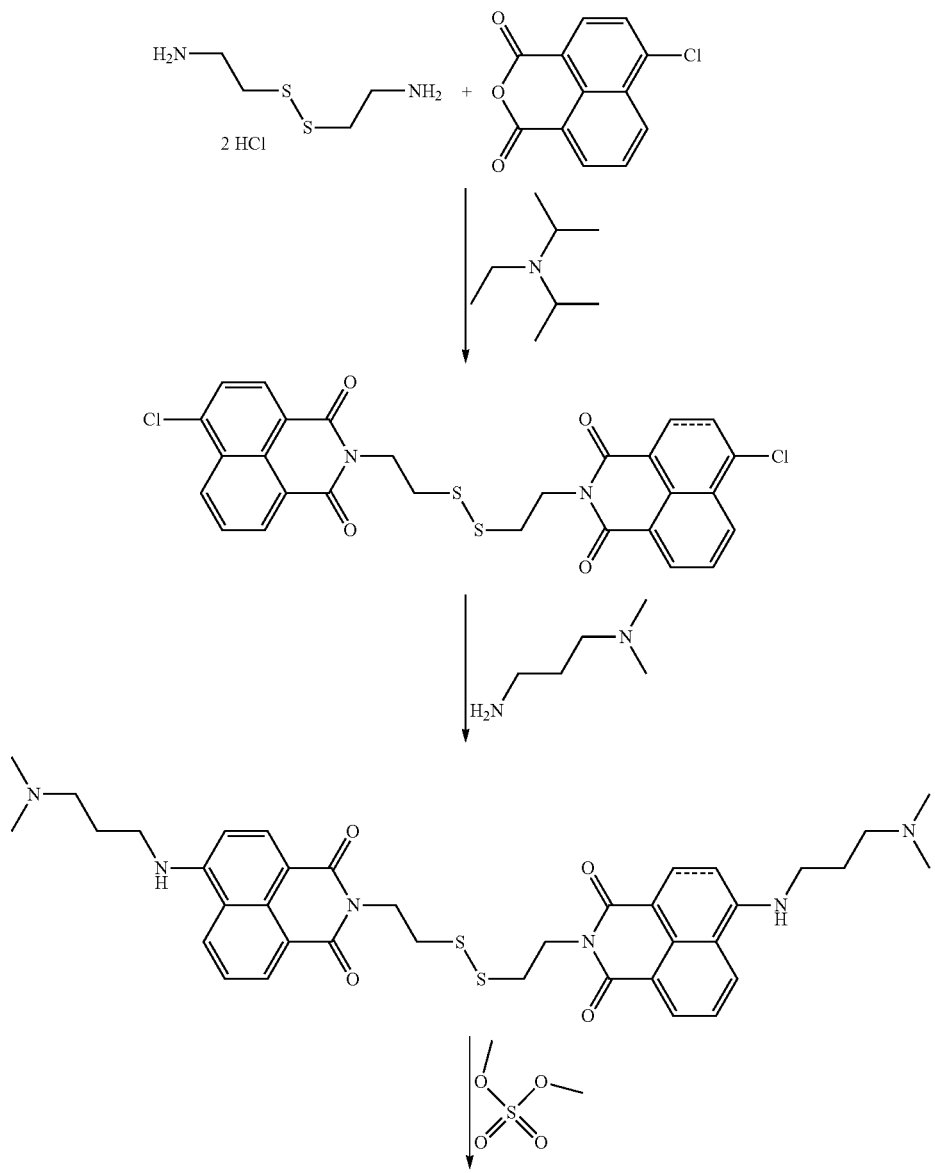

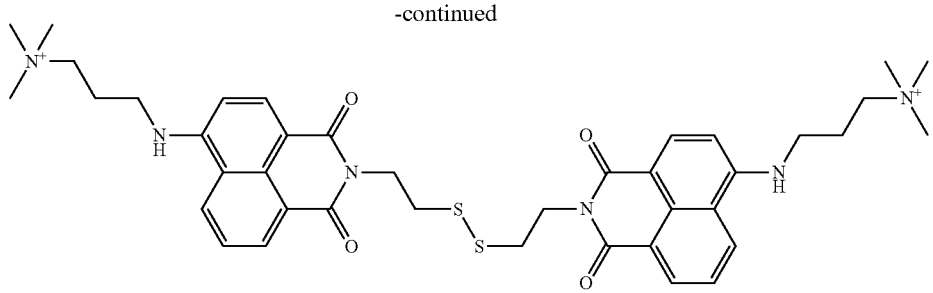

Example 5

Step 1: 2,2'-(Disulphanediyldiethane-2,1-diyl)bis(6-chloro-1H-benzo[de]-isoquinoline-1,3(2H)-dione)

9.30 g of 6-chloro-1H,3H-benzo[de]isochromene-1,3-dione and 4.46 g of hydrochlorided cystamine hydrochloride are suspended in 50 ml of N-methylpyrrolidone (NMP). 5.5 g of diisopropylethylamine are added and the mixture is heated with stirring at 120° C. After two hours, 50 ml of NMP are added and the mixture is kept with stirring at 120° C. for 3 hours. After cooling, the precipitated product is recovered and the filtered solution is extended by addition of 200 ml of water, and a second precipitate is recovered. The precipitates are washed with water and dried. 11.46 g of white powder are recovered. The analyses show that the product is in accordance with the expected product.

Step 2: 2,2'-(Disulphanediyldiethane-2,1-diyl)bis[6-{[3-(dimethylamino)propyl]-amino}-1H-benzo[de]isoquinoline-1,3(2H)-dione]

4 g of (6-chloro-2-(2-{[2-(6-chloro-1,3-dioxo-1H-benzo[de]isoquinolin-2(3H)-yl)ethyl]-disulphanyl}ethyl)-1H-benzo[de]isoquinoline-1,3(2H)-dione are suspended in 40 ml of N,N-dimethylpropane-1,3-diamine. The mixture is heated with stirring at 110° C. for 12 hours. After cooling, a yellow precipitate is collected, and 500 ml of a 1/1 ethanol/water mixture are added dropwise to the filtrate. The yellow paste obtained is isolated and triturated with 200 ml of acetone. The solids obtained are washed with 300 ml of water and dried. 4.5 g of yellow powder are recovered. The analyses show that the product is in accordance with the expected product.

Step 3: 3,3'-{Disulphanediylbis[ethane-2,1-diyl(1,3-dioxo-1H-benzo[de]iso-quinoline-2,6(3H)-diyl)imino]}bis(N,N,N-trimethylpropan-1-aminium)sulphate 4 g of 6-{[3-(dimethylamino)propyl]amino}-2-[2-({2-[6-{[3-(dimethylamino)propyl]-amino}-1,3-dioxo-1H-benzo[de]isoquinolin-2(3H)-yl]ethyl}disulphanyl)ethyl]-1H-benzo-[de]isoquinoline-1,3(2H)-dione are suspended in 50 ml of dimethylformamide. 4 ml of dimethyl sulphate are added and the mixture is kept with stirring at ambient temperature for 4 hours. The reaction mixture is poured into 500 ml of ethyl acetate. The precipitate is filtered off, washed with 4 times 100 ml of ethyl acetate and dried under vacuum. This gives 5.9 g of yellow powder. The analyses indicate that the product is in accordance with the expected product. $^1$H NMR (400 MHz, DMSO-$d_6$): 2.13 (m, 4H), 3.06 (m, 4H), 3.09 (s, 18H), 3.46 (m, 4H), 4.36 (m, 4H), 6.85 (d, 2H), 7.71 (m, 2H), 7.82 (t, 2H), 8.28 (d, 2H), 8.29 (dd, 2H), 8.45 (dd, 2H).

Example 6

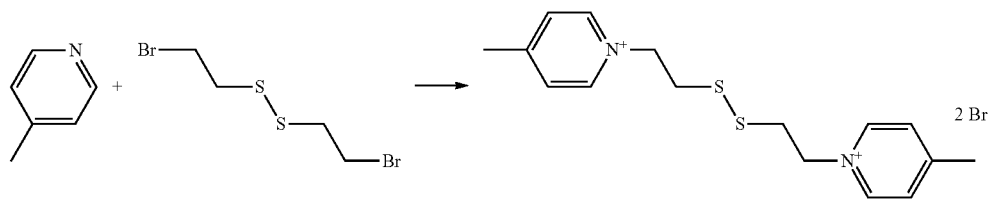

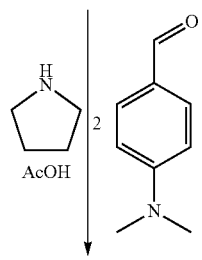

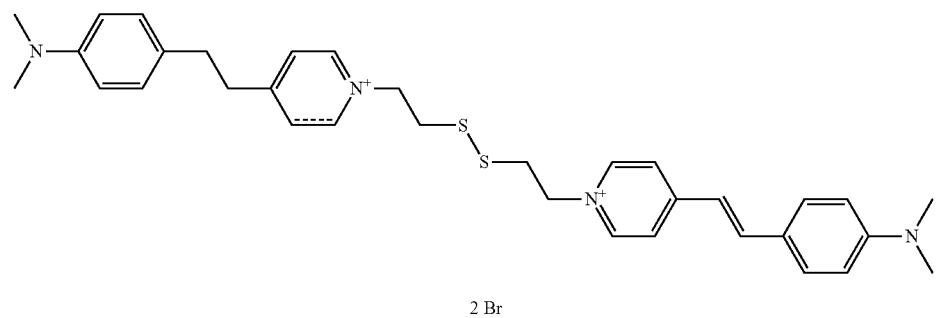

2 Br

Step 1: 1,1'-(Disulphanediyldiethane-2,1-diyl)bis(4-methylpyridinium)dibromide 67 g of 4-picoline are diluted in 100 ml of acetonitrile and the mixture is heated to 80° C. A mixture of 60 g of 1-bromo-2-[(2-bromoethyl)disulphanyl]ethane and 15 ml of N-methylpyrrolidone (NMP) is added over 5 minutes. After 4 hours of stirring at 85° C., the mixture is cooled. The solid obtained is filtered off, rinsed with 3×200 ml of acetonitrile and then dissolved in 800 ml of isopropanol (at reflux). After cooling, 1 l of ethyl ether is added. The precipitate formed is filtered off, rinsed with 3×200 ml of ethyl ether and then dried. The off-white powder obtained (73.77 g) contains a great majority (>90%) of the expected product, which is used as it is for the following step.

Step 2: 1,1'-(Disulphanediyldiethane-2,1-diyl)bis(4-{(E)-2-[4-(dimethylamino)-phenyl]vinyl}pyridinium)dibromide 13.2 g of 4-dimethylaminobenzaldehyde are suspended in 100 ml of methanol. 6.2 g of pyrrolidine and then 5.3 g of acetic acid, diluted in 20 ml of methanol, are added to the mixture (final pH ⅚). 20 g of 1,1'-(disulphanediyldiethane-2,1-diyl)bis(4-methyl-pyridinium) dibromide, obtained in the preceding step, and dissolved in 80 ml of methanol, are introduced, and then the reaction mixture is diluted by addition of 100 ml of methanol. After 21 h of stirring at ambient temperature, a first precipitate is recovered, washed with 3×100 ml of ethanol and then 3×200 ml of ethyl acetate and dried (red powder, 7.4 g), and then a second precipitate, formed in the filtrate, is likewise recovered and dried (red powder, 11.44 g). The analyses indicate that the two fractions are in accordance with the structure expected. $^1$H NMR (400 MHz, MeOH-d$_4$): 3.02 (s, 12H), 3.42 (t, 4H), 4.74 (t, 4H), 6.77 (d, 4H), 7.19 (d, 2H), 7.6 (d, 4H), 7.97 (d, 2H), 8.1 (d, 4H), 8.79 (d, 4H).

Example 7

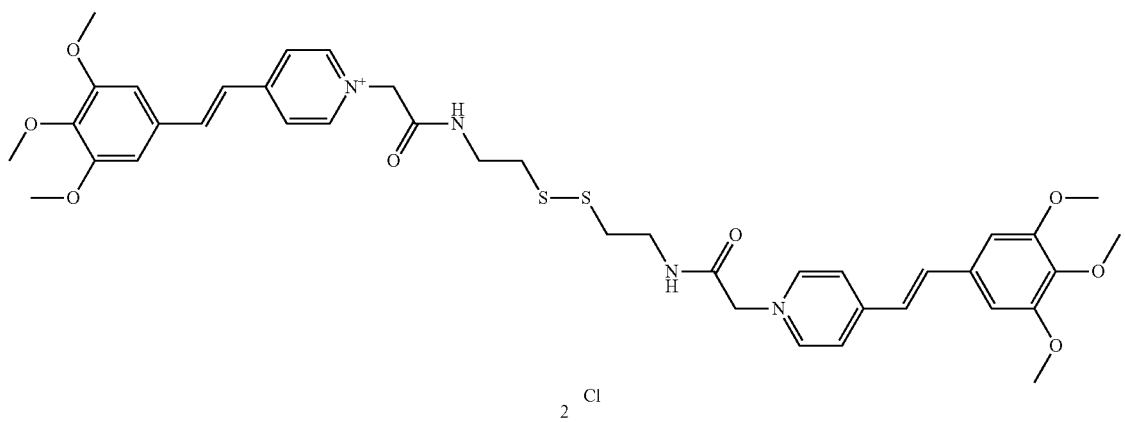

2 Cl

Synthesis Scheme
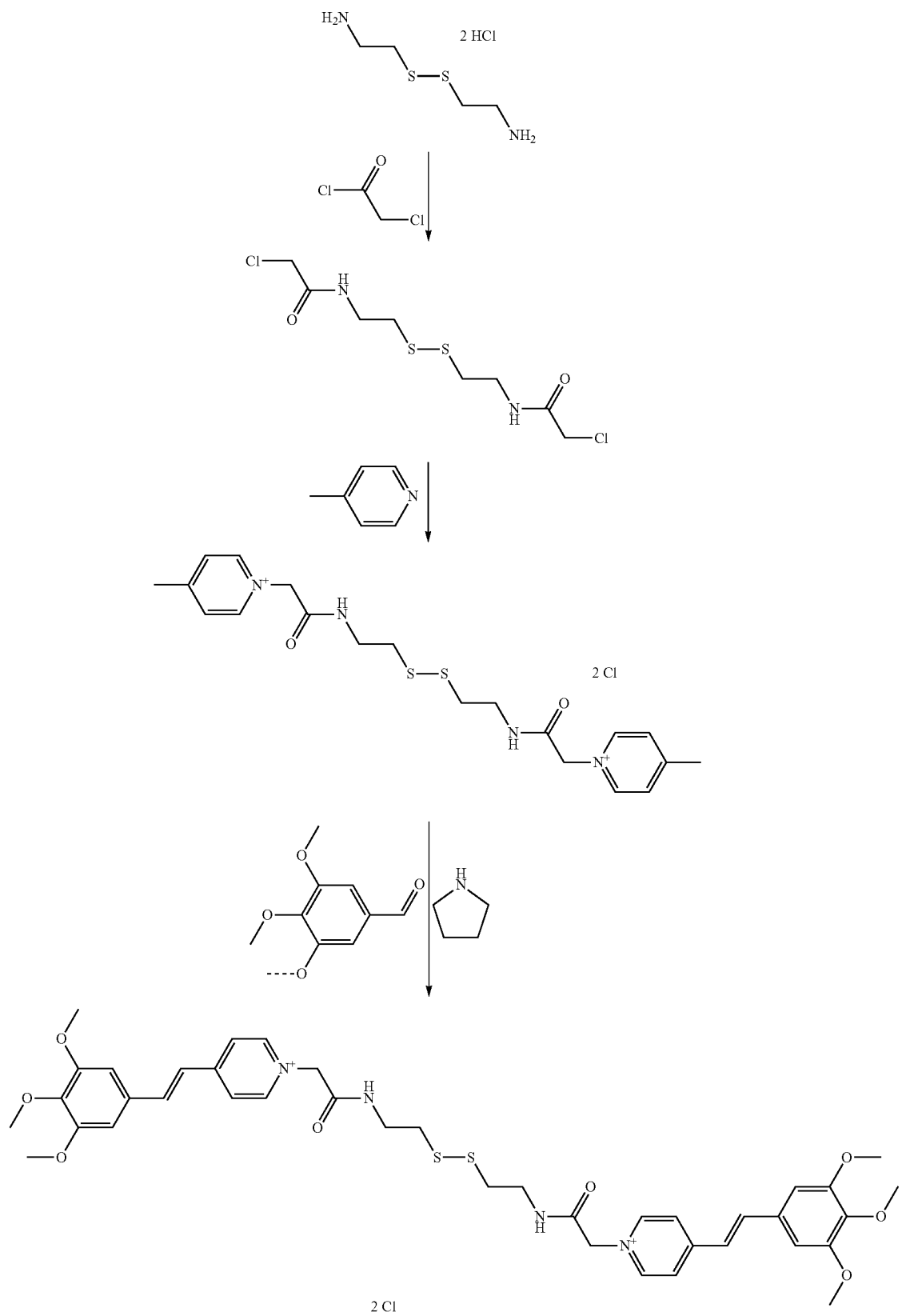

Step 1: Synthesis of N,N'-(disulphanediyldiethane-2,1-diyl)bis(2-chloroacetamide)

40.3 g of cystamine dihydrochloride are dissolved in 100 ml of water, 32 ml of 35% sodium hydroxide solution are added (pH 9.7) and the temperature is lowered to 5° C. 33.5 ml of chloracetyl chloride are introduced dropwise, with the temperature being maintained at less than 10° C. and the pH at between 7.9 and 9.3 by addition of sodium hydroxide solution. The mixture is maintained with stirring at ambient temperature for 2 hours. The precipitate is filtered off, washed with 5×150 ml of water and then dried under vacuum in the presence of $P_2O_5$. 35.3 g of white powder are recovered. The analyses indicate that the product conforms.

Step 2: Synthesis of 1,1'-{disulphanediylbis[ethane-2,1-diylimino(2-oxoethane-2,1-diyl)]}bis(4-methylpyridinium)dichloride 6.1 g of N,N'-(disulphanediyldiethane-2,1-diyl)bis(2-chloroacetamide) and 4.5 g of 4-picoline are dissolved in 50 ml of NMP and the solution is heated at 80° C. for 19 hours. After the mixture has been cooled, 9.2 g of salts are recovered by successive precipitations from acetone and drying under vacuum. The analyses show that the product conforms. $^1$H NMR (400 MHz, $D_2O$): 2.61 (s, 6H), 2.82 (t, 4H), 3.56 (t, 4H), 5.31 (s, 4H), 7.85 (d, 4H), 8.51 (d, 4H).

Step 3: Synthesis of 1,1'-{disulphanediylbis[ethane-2,1-diylimino(2-oxoethane-2,1-diyl)]}bis{4-[(E)-2-(3,4,5-trimethoxyphenyl)vinyl]pyridinium}dichloride[4]

785 mg of 3,4,5-trimethoxybenzaldehyde, 328 µl of pyrrolidine, 232 µl of acetic acid and 490 mg of 1,1'-{disulphanediylbis[ethane-2,1-diylimino(2-oxoethane-2,1-diyl)]}bis-(4-methylpyridinium)dichloride are dissolved in 10 ml of isopropanol and the solution is kept with stirring at ambient temperature for 3 hours 30 minutes. The mixture is poured into 50 ml of a 1:1 dichloromethane/acetone solution. A solid precipitates. It is filtered off, washed with three times 20 ml of acetone and dried under vacuum. 509 mg of black powder are recovered. The analyses show that the product conforms (LCMS: 100%; mass peak m/z=388, corresponding to the dication).

Colouring Examples

Preparation of a Composition A

| | |
|---|---|
| Disulphide dye of formula (I) of the invention | $10^{-3}$ mol % |
| Benzyl alcohol | 4 g |
| Polyethylene glycol 6OE | 6 g |
| Hydroxyethylcellulose | 0.7 g |
| Alkylpolyglucoside in aqueous solution containing 65% active substance | 4.5 g |
| Demineralized water | qs 100 g |

Preparation of a composition B

| | |
|---|---|
| Thioglycolic acid | 1M |
| Sodium hydroxide | qs pH 8.5 |
| Demineralized water | qs 100 g |

At the time of use, the compositions A (9 volumes) and B (1 volume) are mixed and the resulting mixture is then applied to dark hair (tone level 4) for 30 minutes at ambient temperature. After rinsing with water and drying, optical lightening of the hair thus treated is observed.

The locks thus treated are subjected to 30 shampooings in a cycle which comprises the wetting of the locks with water, washing with shampoos, rinsing with water, and then drying.

The lock is dried before the next shampoo is applied.

The colour of the locks before and after 30 washes was evaluated in the L*a*b* system by means of a MINOLTA® CM 2002 spectrophotometer (D65 illuminant).

In the L*a*b* system, the three parameters denote respectively the intensity (L*), the hue (a*) and the saturation (b*). In this system, the higher the value of L, the lighter or less intense the colour, Conversely, the lower the value of L, the darker or greater degree of intensity of the colour a* and b* indicate two colour axes: a* indicates the green/red colour axis, and b* the blue/yellow colour axis.

| | L | a* | b* |
|---|---|---|---|
| Compound 1 | 24.85 | 8.08 | 7.68 |
| Compound 1 after 30 shampooings | 24.78 | 7.83 | 7.56 |
| Compound 2 | 26.32 | 6.38 | 10.01 |
| Compound 2 after 30 shampooings | 25.61 | 5.48 | 9.05 |
| Compound 3 | 25.49 | 10.56 | 9.96 |
| Compound 3 after 30 shampooings | 25.98 | 11.41 | 9.86 |
| Compound 4 | 25.87 | 6.06 | 9.60 |
| Compound 4 after 30 shampooings | 24.38 | 5.86 | 9.20 |
| Compound 5 | 25.08 | 1.19 | 7.51 |
| Compound 5 after 30 shampooings | 25.72 | 1.38 | 6.01 |

The results in the table above show that the colouring changes very little even after 30 shampooings. Thus the colouring and the lightening effect on the hair remains virtually unchanged, hence indicating very good shampooing resistance on the part of the dyes of the invention.

The invention claimed is:

1. A method of coloring dark keratin fibers, possessing a tone level of less than or equal to 6, comprising applying to said dark keratin fibers a dyeing composition comprising, in an appropriate cosmetic medium, at least one fluorescent disulphide entity and simultaneously applying to the dark keratin fibers at least one reducing agent, wherein the at least one fluorescent disulphide entity is selected from the entities of formula (I):

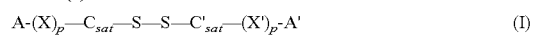

the organic and inorganic acid salts, optical isomers and geometrical isomers, and the solvates thereof;

wherein:

A and A', which are identical, each represent a radical containing at least one cationic fluorescent chromophore;

X and X', which are identical or different, each represent a saturated or unsaturated, linear or branched $C_1$-$C_{30}$ hydrocarbon chain which is optionally interrupted and/or optionally terminated at one or two of its ends by at least one divalent group selected from:
—N(R)—, —N$^+$(R)(R)—, —O—, —S—, —CO—, and —SO$_2$—, wherein radicals R, which are identical or different, are each selected from hydrogen or $C_1$-$C_4$ alkyl, hydroxyalkyl and aminoalkyl radicals; and saturated or unsaturated, fused or non-fused, aromatic or non-aromatic (hetero)cyclic radicals optionally comprising at least one identical or non-identical heteroatom and optionally substituted;
p and p', which are identical or different, are each 0 or 1; and
—$C_{sat}$ and $C'_{sat}$, which are identical or different, each represent an optionally cyclic, optionally substituted, linear or branched $C_1$-$C_{18}$ alkylene chains.

2. The method according to claim 1, wherein X and X', which are identical or different, represent a group —N(R)—, wherein the radicals R, which are identical or different, are selected from hydrogen or $C_1$-$C_4$ alkyl, hydroxyalkyl and aminoalkyl radicals.

3. The method according to claim 1, wherein A and A', which are identical, represent W—C(R$^c$)=C(R$^d$)—Ar— or —W—C(R$^c$)=C(R$^d$)—Ar, and further wherein
W represents a heterocycle or a heteroaryl containing a quaternary ammonium;
Ar represents a 5- or 6-membered (hetero)aryl radical of phenyl or pyridinium type, or a (hetero)aromatic bicyclic radical of naphthyl, benzopyridinium, indolinyl or benzoindolinyl type, optionally substituted by at least one halogen atom, alkyl group, hydroxyl group, alkoxy group, hydroxyalkyl group, amino or (di)alkylamino group, acylamino group; or one 5- or 6-membered heteroaryl or heterocycloalkyl group; and
R$^c$ and R$^d$, which are identical or different, each represent a hydrogen atom or a $C_1$-$C_4$ alkyl group.

4. The method according to claim 3, wherein W is chosen from imidazolium, pyridinium, benzopyridinium, benzimidazolium, quinolinium and pyrazolium.

5. The method according to claim 1, wherein the at least one fluorescent disulphide entity is selected from compounds of formula (VI):

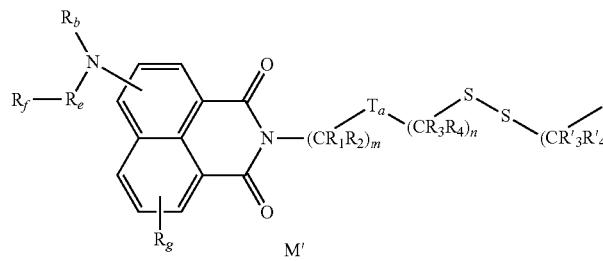
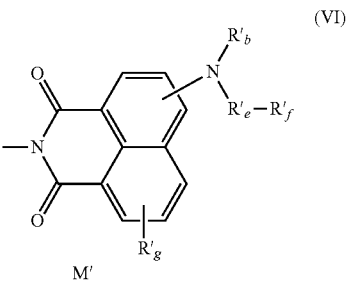

(VI)

wherein
R$_b$ and R'$_b$, which are identical or different, each represent a hydrogen atom, an aryl($C_1$-$C_4$)alkyl group or a $C_1$-$C_6$ alkyl group which is optionally substituted;

R$_e$ and R'$_e$, which are identical or different, each represent a divalent, linear or branched, optionally unsaturated $C_1$-$C_6$ alkylenyl hydrocarbon chain;

R$_f$ and R'$_f$, which are identical or different, each represent a quaternary ammonium group (R")(R''')(R'''')N$^+$ wherein R", R''' and R'''', which are identical or different, each represent a hydrogen atom or a $C_1$-$C_4$ alkyl group, or (R")(R''')(R'''')N$^+$— represents an optionally substituted cationic heteroaryl group, which is optionally substituted by a $C_1$-$C_3$ alkyl group;

R$_g$, R'$_g$, which are identical or different, each represent a hydrogen atom, a halogen atom, an amino, $C_1$-$C_4$ alkylamino, $C_1$-$C_4$ dialkylamino, cyano, carboxyl, hydroxyl or trifluoromethyl group, an acylamino, $C_1$-$C_4$ alkoxy, $C_2$-$C_4$ (poly)hydroxyalkoxy, alkylcarbonyloxy, alkoxycarbonyl or alkylcarbonylamino radical, an acylamino, carbamoyl or alkylsulphonylamino radical, an aminosulphonyl radical, or a $C_1$-$C_{16}$ alkyl radical optionally substituted by a group selected from $C_1$-$C_{12}$ alkoxy, hydroxyl, cyano, carboxyl, amino, $C_1$-$C_4$ alkylamino and $C_1$-$C_4$ dialkylamino, or the two alkyl radicals carried by the nitrogen atom of the amino group form a heterocycle containing 5 to 7 members and optionally comprising another heteroatom which is identical to or different from that of the nitrogen atom;

or two groups R$_g$ and R'$_g$; carried by two adjacent carbon atoms, together form a benzo or indeno ring or a fused heteroaryl or fused heterocycloalkyl group, the benzo, indeno, heterocycloalkyl or heteroaryl ring being optionally substituted by a halogen atom, an amino, $C_1$-$C_4$ alkylamino, $C_4$ dialkylamino, nitro, cyano, carboxyl, hydroxyl or trifluoromethyl group, an acylamino, $C_1$-$C_4$ alkoxy, $C_2$-$C_4$ (poly)hydroxyalkoxy, alkylcarbonyloxy, alkoxycarbonyl, or alkylcarbonylamino radical, an acylamino, carbamoyl or alkylsulphonylamino radical, an aminosulphonyl radical, or a $C_1$-$C_{16}$ alkyl radical which is optionally substituted by a group selected from $C_1$-$C_{12}$ alkoxy, hydroxyl, cyano, carboxyl, amino, $C_1$-$C_4$ alkylamino and $C_1$-$C_4$ dialkylamino; or the two alkyl radicals carried by the nitrogen atom of the amino group form a heterocycle containing 5 to 7 members and optionally comprising another heteroatom identical to or different from that of the nitrogen atom;

—R$_1$, R$_2$, R$_3$, R$_4$, R'$_1$, R'$_2$, R'$_3$ and R'$_4$, which are identical or different, each represent a hydrogen atom or a $C_1$-$C_4$ alkyl, $C_1$-$C_{12}$ alkoxy, hydroxyl, cyano, carboxyl, amino, $C_1$-$C_4$ alkylamino or $C_1$-$C_4$ dialkylamino group, it being possible for said alkyl radicals to form, with the nitrogen atom which carries them, a heterocycle containing 5 to 7 members, optionally comprising another heteroatom different or not different from nitrogen;

T$_a$ and T$_b$, which are identical or different, represent: i) a covalent a bond; ii) at least one radical selected from —SO$_2$—, —O—, —S—, —N$^+$(R)(R$^o$)—, and —CO—; wherein R and R$^o$, which are identical or different, represent a hydrogen atom or a $C_1$-$C_4$ alkyl or $C_1$-$C_4$ hydroxyalkyl radical, or an aryl($C_1$-$C_4$)alkyl; or iii) a cationic or non-cationic heteroaryl or heterocycloalkyl radical;

m, m', n and n', which are identical or different, represent an integer ranging from 0 to 6, wherein m+n and m'+n', and which are identical or different, each represents an integer ranging from 1 to 10; and M' represents a counterion or an organic or inorganic acid salt.

6. The method according to claim 5, wherein at least one of $R_f$ or $R'_f$ represents an imidazolinium group.

7. The method according to claim 1, wherein the at least one fluorescent disulphide entity is selected from:

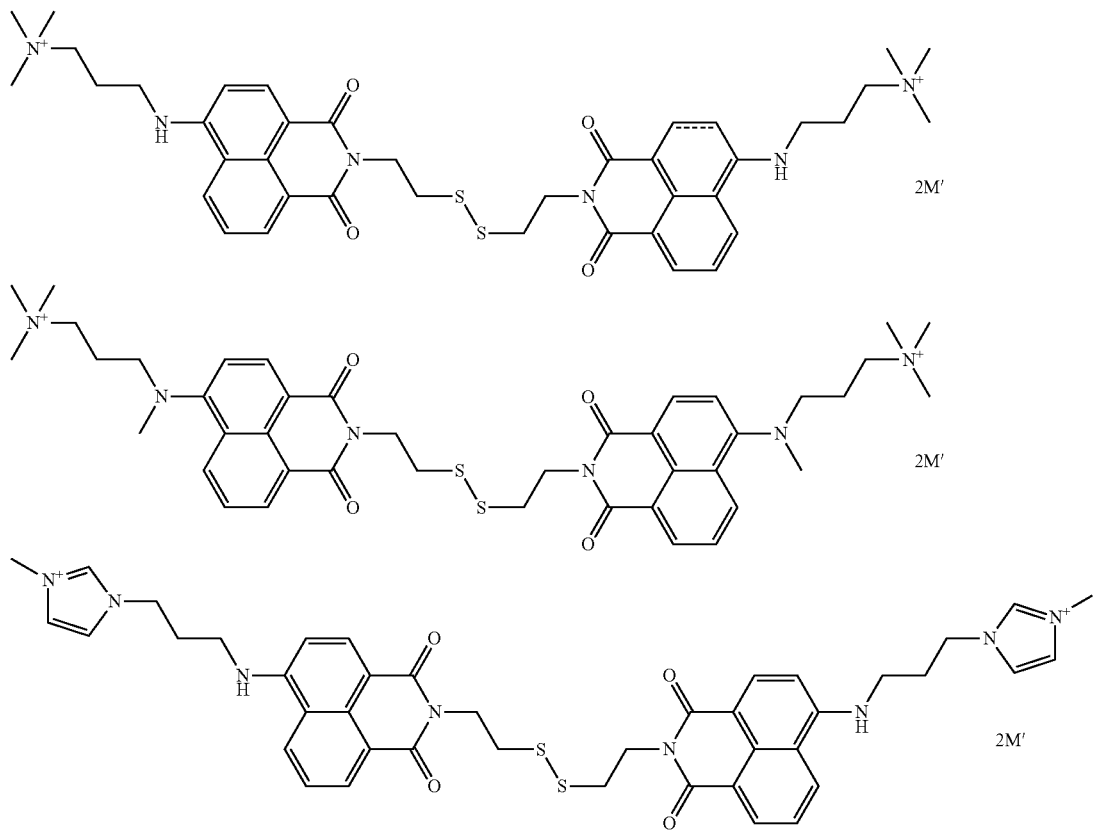

wherein M' is an anionic counterion.

8. The method according to claim 1, wherein the at least one reducing agent is selected from: cysteine, homocysteine, thiolactic acid, and salts thereof; phosphines; bisulphite; sulphites; and thioglycolic acid and esters of thioglycolic acid.

9. The method according to claim 1, wherein the dark keratin fibers possess a tone level of less than or equal to 4.

10. The method according to claim 1, further comprising applying at least one oxidizing agent to the keratin fibers.

11. The method according to claim 1, wherein the at least one fluorescent disulphide entity is present in an amount ranging from 0.001% to 50% by weight, relative to the total weight of the dyeing composition.

12. The method according to claim 11, wherein the at least one fluorescent disulphide entity is present in an amount ranging from 0.005% to 20% by weight, relative to the total weight of the dyeing composition.

13. The method according to claim 12, wherein the at least one fluorescent disulphide entity is present in an amount ranging from 0.01% to 5% by weight, relative to the total weight of the dyeing composition.

14. A multicompartment device comprising at least one first compartment comprising a dyeing composition for dark keratin fibers possessing a tone level of less than or equal to 6, comprising at least one fluorescent disulphide entity chosen from formula (I):

$$A\text{-}(X)_p\text{—}C_{sat}\text{—}S\text{—}S\text{—}C'_{sat}\text{—}(X')_p\text{-}A \qquad (I)$$

the organic and inorganic acid salts, optical isomers and geometrical isomers, and the solvates thereof;

wherein:

A and A', which are identical, each represents a radical containing at least one cationic fluorescent chromophore;

X and X', which are identical or different, each represent a saturated or unsaturated, linear or branched $C_1$-$C_{30}$ hydrocarbon chain which is optionally interrupted and/or optionally terminated at one or two of its ends by at least one divalent group selected from:

—N(R)—, —N⁺(R)(R)—, —O—, —S—, —CO—, and —$SO_2$—, wherein radicals R, which are identical or different, are each selected from hydrogen or $C_1$-$C_4$ alkyl, hydroxyalkyl and aminoalkyl radicals; and saturated or unsaturated, fused or non-fused, aromatic or non-aromatic (hetero)cyclic radicals optionally comprising at least one identical or non-identical heteroatom and optionally substituted;

p and p', which are identical or different, are each 0 or 1;

—$C_{sat}$ and $C'_{sat}$, which are identical or different, each represent an optionally cyclic, optionally substituted, linear or branched $C_1$-$C_{18}$ alkylene chains; and at least one second compartment comprising at least one reducing agent.

15. A method of lightening dark keratin fibers possessing a tone level of less than or equal to 6, comprising applying to said dark keratin fibers a dyeing composition comprising, in an appropriate cosmetic medium, at least one fluorescent disulphide entity and simultaneously applying to said dark keratin fibers at least one reducing agent, wherein the at least one fluorescent disulphide entity is selected from the entities of formula (I) and:

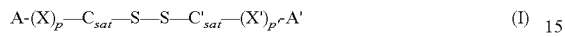

$$A\text{-}(X)_p\text{—}C_{sat}\text{—}S\text{—}S\text{—}C'_{sat}\text{—}(X')_{p'}\text{-}A' \quad (I)$$

the organic and inorganic acid salts, optical isomers and geometrical isomers, and the solvates thereof;

wherein:

A and A', which are identical, each represents a radical containing at least one cationic fluorescent chromophore;

X and X', which are identical or different, each represent a saturated or unsaturated, linear or branched $C_1$-$C_{30}$ hydrocarbon chain which is optionally interrupted and/or optionally terminated at one or two of its ends by at least one divalent group selected from:

—N(R)—, —N$^+$(R)(R)—, —O—, —S—, —CO—, and —SO$_2$—, wherein radicals R, which are identical or different, are each selected from hydrogen or $C_1$-$C_4$ alkyl, hydroxyalkyl and aminoalkyl radicals; and saturated or unsaturated, fused or non-fused, aromatic or non-aromatic (hetero)cyclic radicals optionally comprising at least one identical or non-identical heteroatom and optionally substituted;

p and p', which are identical or different, are each 0 or 1; and $C_{sat}$ and $C'_{sat}$, which are identical or different, each represent an optionally cyclic, optionally substituted, linear or branched $C_1$-$C_{18}$ alkylene chains.

* * * * *

UNITED STATES PATENT AND TRADEMARK OFFICE
CERTIFICATE OF CORRECTION

PATENT NO. : 8,328,880 B2  
APPLICATION NO. : 13/232452  
DATED : December 11, 2012  
INVENTOR(S) : Nicolas Daubresse et al.

It is certified that error appears in the above-identified patent and that said Letters Patent is hereby corrected as shown below:

Claim 5, column 78, line 65, change "covalent a" to -- covalent σ --.

Signed and Sealed this
Twenty-sixth Day of February, 2013

Teresa Stanek Rea
*Acting Director of the United States Patent and Trademark Office*